(12) United States Patent
Terashima

(10) Patent No.: US 11,666,783 B2
(45) Date of Patent: Jun. 6, 2023

(54) VASCULAR MARKER FOR RADIOTHERAPY, RADIOTHERAPY ASSISTANCE METHOD, RADIATION IRRADIATION CONTROL DEVICE, AND VASCULAR MARKER INDWELLING ASSISTANCE DEVICE

(71) Applicant: Kazuki Terashima, Osaka (JP)

(72) Inventor: Kazuki Terashima, Osaka (JP)

(*) Notice: Subject to any disclaimer, the term of this patent is extended or adjusted under 35 U.S.C. 154(b) by 119 days.

(21) Appl. No.: 16/634,473

(22) PCT Filed: Jul. 25, 2018

(86) PCT No.: PCT/JP2018/027982
§ 371 (c)(1),
(2) Date: Jan. 27, 2020

(87) PCT Pub. No.: WO2019/022168
PCT Pub. Date: Jan. 31, 2019

(65) Prior Publication Data
US 2020/0254280 A1 Aug. 13, 2020

(30) Foreign Application Priority Data

Jul. 25, 2017 (JP) .............................. JP2017-144043
Aug. 25, 2017 (JP) .............................. JP2017-162227

(51) Int. Cl.
*A61N 5/10* (2006.01)
*A61B 90/00* (2016.01)

(52) U.S. Cl.
CPC ............ *A61N 5/1049* (2013.01); *A61B 90/39* (2016.02); *A61N 5/1067* (2013.01);
(Continued)

(58) Field of Classification Search
CPC .... A61N 5/1049; A61N 5/1069; A61N 5/107; A61N 2005/1061; A61N 2005/1062;
(Continued)

(56) References Cited

U.S. PATENT DOCUMENTS 6,306,153 B1 * 10/2001 Kurz ................ A61B 17/12022
606/191
6,356,782 B1 * 3/2002 Sirimanne .............. A61B 90/39
600/431
(Continued)

FOREIGN PATENT DOCUMENTS

JP 9-168541 A 6/1997
JP 2001-50221 A 2/2001
(Continued)

OTHER PUBLICATIONS

"Spring." Merriam-Webster.com Dictionary, Merriam-Webster, https://www.merriam-webster.com/dictionary/spring. Accessed Dec. 10, 2021. (Year: 2021).*
(Continued)

*Primary Examiner* — Carrie R Dorna
(74) *Attorney, Agent, or Firm* — Sheppard Mullin Richter & Hampton LLP

(57) ABSTRACT

A more accurate radiotherapy is implemented by using a vessel marker for radiotherapy having a deformation fixed shape for engaging with the inner wall of a vessel by deformation after being inserted into the vessel, and a position notification shape for notifying an outside of a radiation irradiation position. Also provided are a radiotherapy support method for supporting radiotherapy to be performed by using the vessel marker, a radiation irradiation control apparatus that irradiates, with radiation, a patient in
(Continued)

which the vessel marker is indwelled, and a vessel marker indwelling support apparatus to be used when indwelling the vessel marker.

13 Claims, 20 Drawing Sheets

(52) U.S. Cl.
CPC .............. *A61B 2090/3904* (2016.02); *A61B 2090/3937* (2016.02); *A61B 2090/3966* (2016.02); *A61N 2005/1052* (2013.01); *A61N 2005/1061* (2013.01)

(58) Field of Classification Search
CPC ............ A61B 90/39; A61B 2090/3904; A61B 2090/3908; A61B 2090/3912; A61B 2090/3966; A61B 2090/3983; A61F 2/2475
See application file for complete search history.

(56) References Cited

U.S. PATENT DOCUMENTS

| | | | | |
|---|---|---|---|---|
| 6,994,712 | B1* | 2/2006 | Fisher | A61B 90/39 606/116 |
| 2003/0078465 | A1* | 4/2003 | Pai | A61B 17/064 600/16 |
| 2004/0097981 | A1* | 5/2004 | Seiis | A61B 90/39 606/151 |
| 2006/0093089 | A1* | 5/2006 | Vertatschitsch | A61N 5/1049 378/65 |
| 2007/0083226 | A1 | 4/2007 | Buiser et al. | |
| 2007/0112423 | A1* | 5/2007 | Chu | A61F 2/2445 623/2.11 |
| 2012/0046928 | A1* | 2/2012 | Gibbs | A61N 5/1049 703/11 |
| 2016/0158577 | A1* | 6/2016 | Escarguel | A61B 90/39 600/1 |

FOREIGN PATENT DOCUMENTS

| | | |
|---|---|---|
| JP | 2001-502221 A | 2/2001 |
| JP | 2015-24024 A | 2/2015 |
| JP | 2015-142671 A | 8/2015 |
| JP | 2019-24587 A | 2/2019 |

OTHER PUBLICATIONS

Japanese Office Action (Notice of Reasons for Refusal) with an English translation dated Mar. 30, 2018 for Application No. JP 2017-144043.
Japanese Office Action (Notice of Reasons for Refusal) with an English translation dated Mar. 30, 2018 for Application No. JP 2017-162227.
International Search Report (ISR) and Written Opinion (WO) dated Oct. 16, 2018 for Application No. PCT/JP2018/027982.
Japanese Office Action (Decision of Refusal) with an English translation dated Dec. 17, 2018 for Application No. JP 2017-144043.
Akio Sumita, Yasunori Taguchi, "Moving Body Tracking System for Heavy Particle Beam Cancer Therapy", Isotope News, Jan. 2015, No. 729, pp. 28-30.
Kenji Horita, "Experience of Using New Moving Body Tracking System SyncTraX", Public Interest Incorporated Association, Japanese Society of Radiological Technology, Radiotherapy Section Journal, vol. 29, No. 1, Apr. 2015.
Masumi Umezawa et al., "Development of Compact Proton Beam Therapy System for Moving Organs", Hitachi Review, vol. 97, No. 06-07, Innovative R & D Report 2015, pp. 70-75.
Rha, Seung-Woon, "Peripheral Coil Embolization; Tips and Tricks", Encore Seoul 2015, Sep. 17, 2015, p. 65-68.
Japanese Office Action (Notice of Reasons for Refusal) with an English translation dated Mar. 26, 2020 for corresponding Japanese Application No. JP 2017-144043.
Boston Scientific, "Peripheral Embolization Products Product Catalog and Ordering Information", 2014 year 3 month, p. 1-17.
Cook Embolization Coil(Hilal ABC), August issue, 2015 (fifth edition), p. 1-2.
Shimizu, Masakazu et al., "The Usefulness of Using Fiducial Marker in Proton Therapy for Locally Advanced Pancreatic Cancer", Japanese journal of radiological technology, 2016, vol. 72, No. 11, p. 1074 1083.
Karaman Kutlay et al., "Intravascular Placement of Metallic Coils as Lung Tumor Markers for CyberKnife Stereotactic Radiation Therapy", Korean Journal of Radiology, 2015, vol. 16,No. 3, pp. 626-631.
Young, Shamar et al., Transarterial Fiducial Marker Placement: A Novel Technique, Journal of Vascular and Interventional Radiology, 2013, vol. 24, No. 5, pp. 756-758.
Ohta, K. et al., "Educational Exhibit Abstract No. 407-Transarterial fiducial marker placement for proton therapy of malignant liver tumors", Journal of Vascular and Interventional Radiology, 2014, vol. 25, No. 3, supplement, p. S178.
English abstract of JP 2001-502221 A.

\* cited by examiner

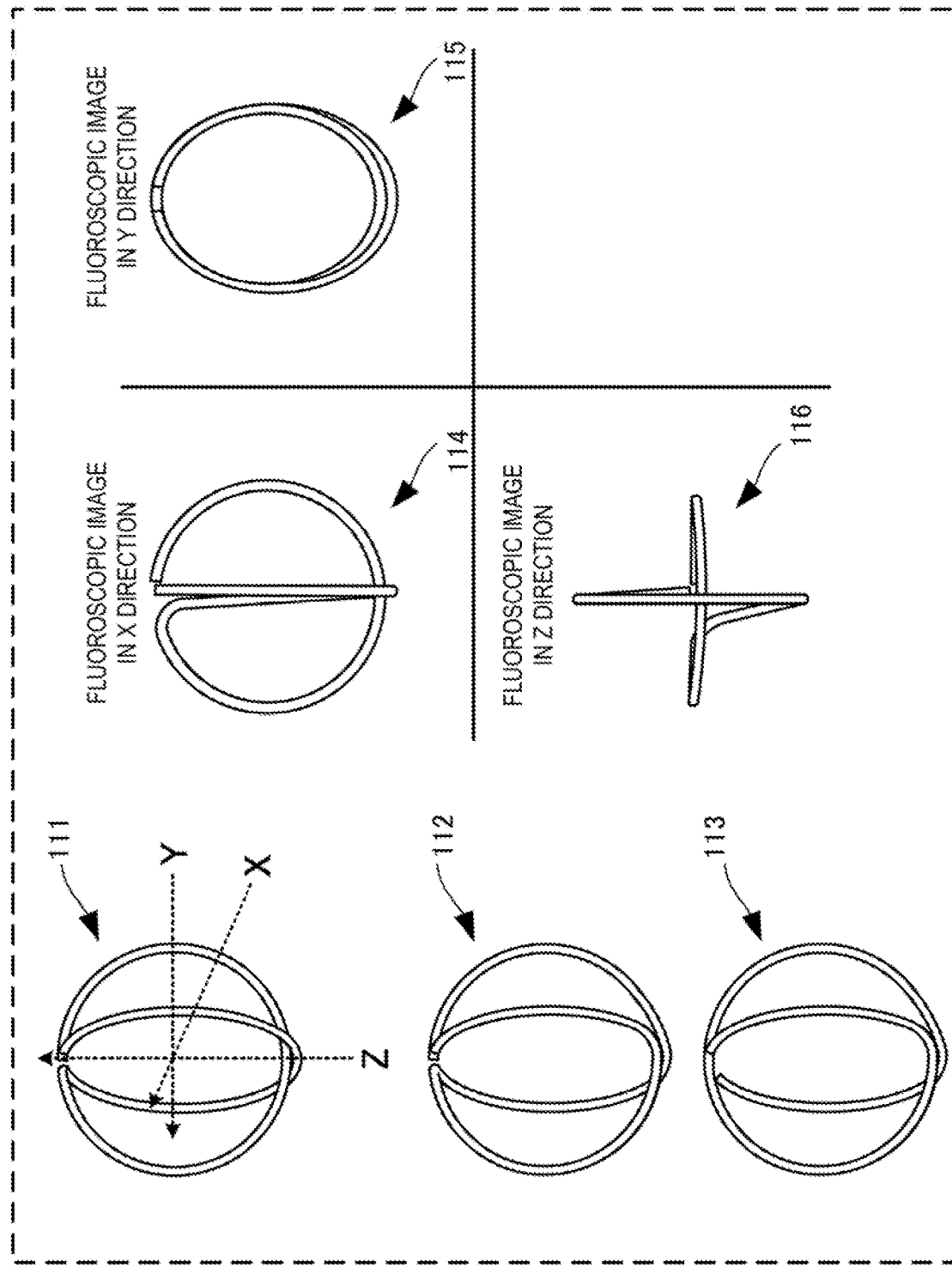

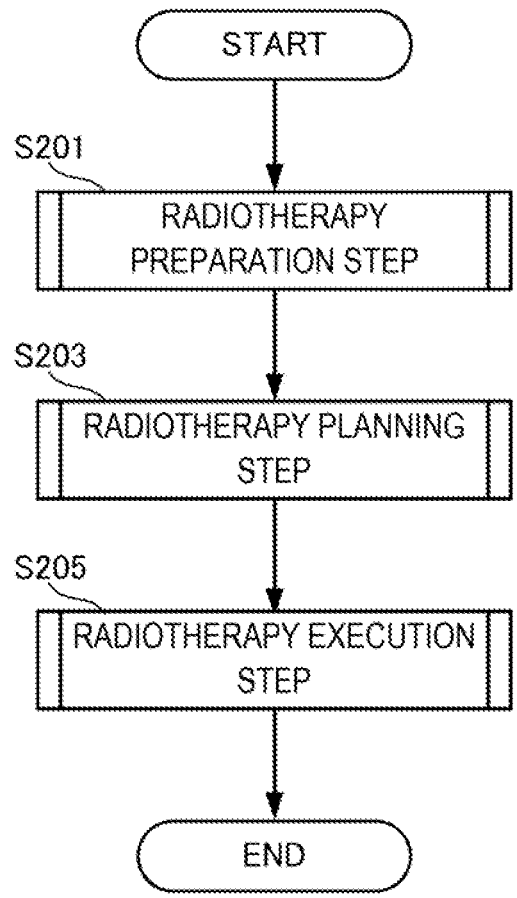
F I G. 2A

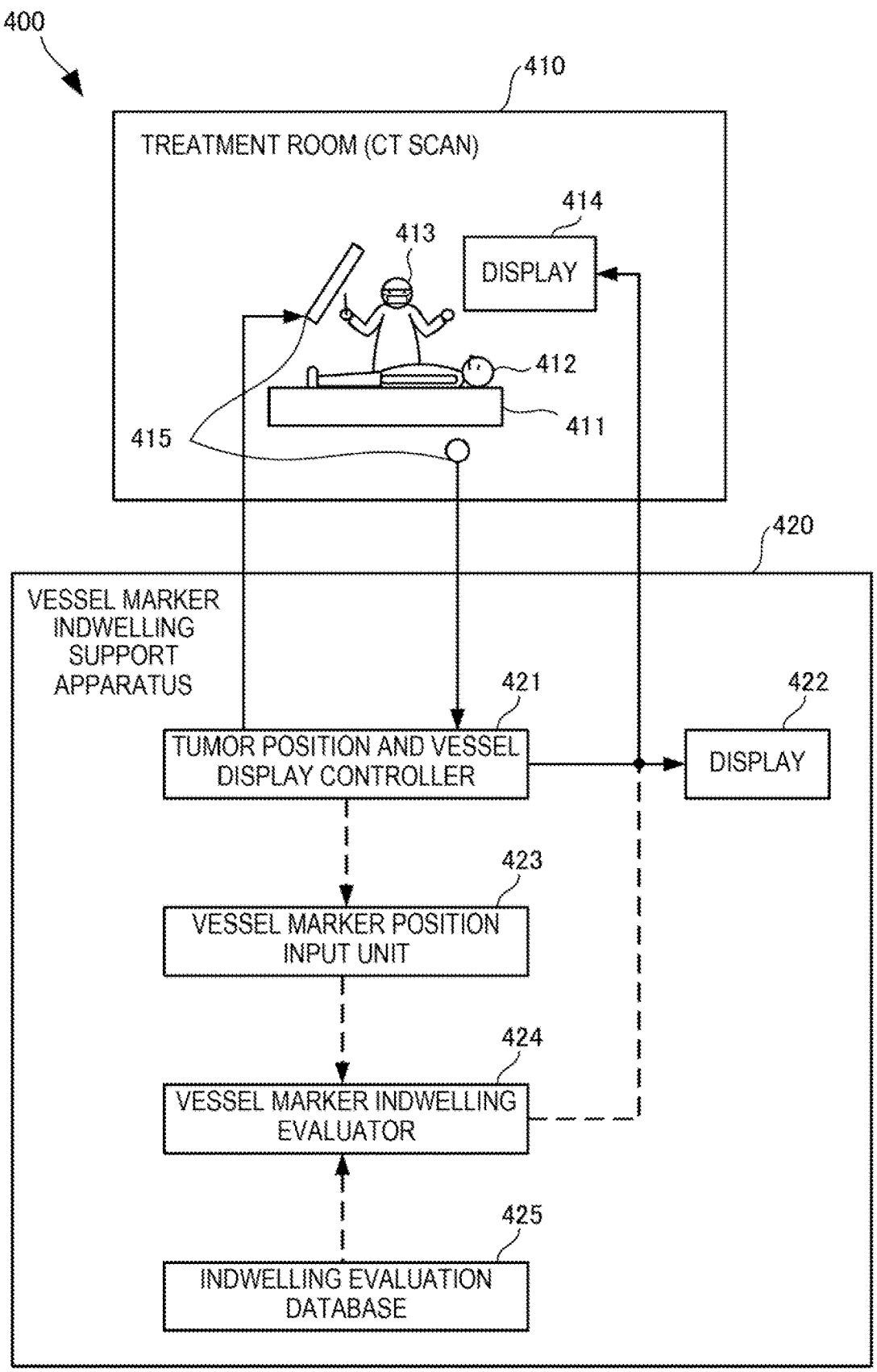
F I G. 4

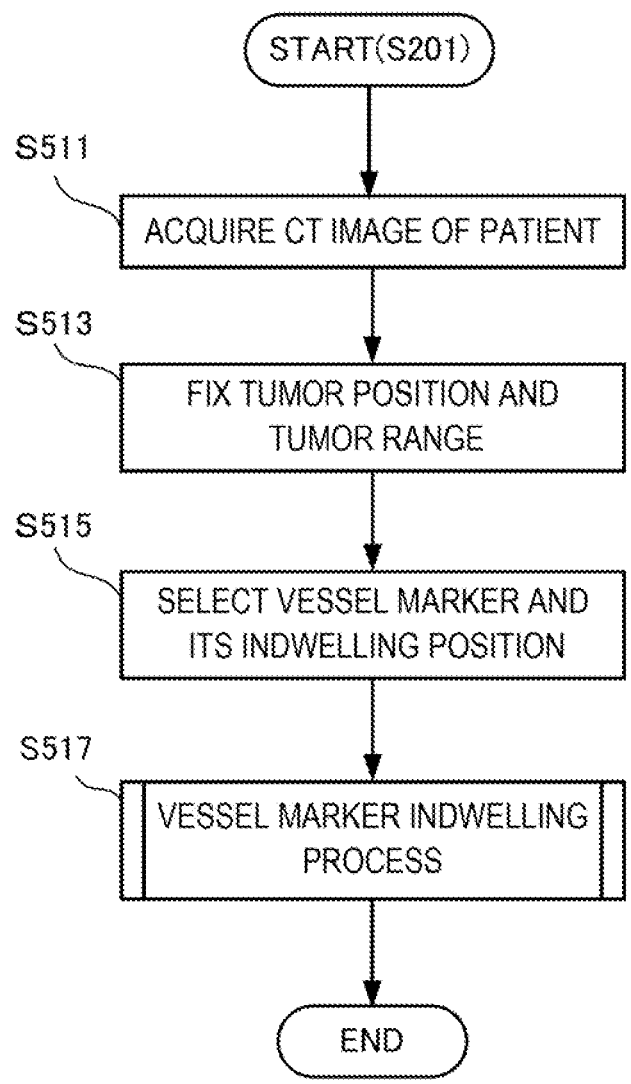
F I G. 5A

FIG. 10

| TUMOR POSITION | | VESSEL MARKER INDWELLING INFORMATION 1002 | | | VESSEL MARKER INDWELLING INFORMATION 1003 | | | VESSEL MARKER INDWELLING INFORMATION 1004 | | | ... |
|---|---|---|---|---|---|---|---|---|---|---|---|
| AFFECTED PART | REGION | VESSEL MARKER | BLOOD VESSEL NAME | INDWELLING RANGE | VESSEL MARKER | BLOOD VESSEL NAME | INDWELLING RANGE | VESSEL MARKER | BLOOD VESSEL NAME | INDWELLING RANGE | |
| | | | | | | | | | | | |
| | | | ... | | ... | | | | | | |
| ... | ... | | | | | | | | | | |
| ... | ... | | | | | | | | | | |

| VESSEL MARKER ID (1311) | SHAPE (1312) | DIMENSIONS (1313) | IMAGE DATA (1314) | ... |
|---|---|---|---|---|
| 0010 | S SHAPE | 2mm × 3mm | | |
| 0011 | S SHAPE | 5mm × 3mm | | |
| ⋮ | | | | |
| 0020 | DOUBLE CIRCLE | 2mm/3mm | | |
| 0021 | DOUBLE CIRCLE | 5mm/3mm | | |
| ⋮ | | | | |
| 0030 | | 2mm DIAMETER | | |
| 0031 | | 3mm DIAMETER | | |
| ⋮ | | | | |
| 0040 | | 2mm × 3mm | | |
| 0041 | | 3mm × 5mm | | |
| ⋮ | | | | |

1320

| DISCRIMINATED VESSEL MARKER ID (1321) | THREE-DIMENSIONAL POSITION (X, Y, AND Z COORDINATES) (1322) | ... | CALCULATED TUMOR POSITION (1323) | CALCULATED BED POSITION (1324) |
|---|---|---|---|---|
| 0010 | | | | |
| 0021 | | | | |
| ⋮ | | | | |

VASCULAR MARKER FOR RADIOTHERAPY, RADIOTHERAPY ASSISTANCE METHOD, RADIATION IRRADIATION CONTROL DEVICE, AND VASCULAR MARKER INDWELLING ASSISTANCE DEVICE

RELATED APPLICATIONS

This application is an application under 35 U.S.C. 371 of International Application No. PCT/JP2018/027982 filed on Jul. 25, 2018, the entire contents of which are incorporated herein by reference.

This application is based upon and claims the benefit of priorities from Japanese Patent Applications No. 2017-144043 filed on Jul. 25, 2017 and No. 2017-162227 filed on Aug. 25, 2017, the disclosure of which is incorporated herein in its entirely by reference.

TECHNICAL FIELD

The present invention relates to a vessel marker for radiotherapy and its peripheral technology.

BACKGROUND ART

Treatment methods that emit radiation including an X-ray, an electron beam, a proton beam, and a heavy particle beam (carbon ion beam) are widely used in therapies of cancers (malignant tumors) because the load on a body is small and side effects are few compared to surgical operations. In the abovementioned technical field, patent literatures 1 and 2 disclose techniques that determine a radiation irradiation position by using a metal marker indwelled in the living body of a patient. Also, non-patent literatures 1 to 3 disclose methods of percutaneously needling and indwelling a metal marker.

CITATION LIST

Patent Literatures

Patent literature 1: Japanese Patent Laid-Open No. 2015-142671
Patent literature 2: Japanese Patent Laid-Open No. 2015-024024

NON-PATENT LITERATURES

Non-patent literature 1: Akio Sumita, Yasunori Taguchi, "Moving Body Tracking System for Heavy Particle Beam Cancer Therapy", Isotope News, January 2015, No. 729, pp. 28-30
Non-patent literature 2: Kenji Horita, "Experience of Using New Moving Body Tracking System SyncTraX", Public Interest Incorporated Association, Japanese Society of Radiological Technology, Radiotherapy Section Journal, Vol. 29, No. 1, April 2015
Non-patent literature 3: Masumi Umezawa et al., "Development of Compact Proton Beam Therapy System for Moving Organs", Hitachi Review, Vol. 97, No. 06-07, Innovative R & D Report 2015, pp. 70-75

SUMMARY OF THE INVENTION

Technical Problem

In the techniques described in the above literatures, however, a metal marker is percutaneously needled and indwelled. Therefore, bones, blood vessels, and organs that are not therapy targets must be avoided from the needling path, and this limits the metal marker indwelling portion. Also, the invasiveness is high because an organ is directly needled, and this increases the crisis rate of complications (intraorgan bleeding, intraabdominal bleeding, intrapleural bleeding, pneumothorax, tumor dissemination, and the like). Furthermore, the fixability of the metal marker changes due to the tissue density of the indwelling portion, and the metal marker often comes out into the blood vessel or the abdominal cavity.

The present invention provides a technique that solves the above-described problems.

Solution to Problem

One example aspect of the present invention provides a vessel marker for radiotherapy, comprising a deformation fixed shape for engaging with an inner wall of a vessel by deformation after being inserted into the vessel, and a position notification shape for notifying an outside of a radiation irradiation position.

Another example aspect of the present invention provides a radiotherapy support method comprising:
inserting a vessel marker into a vessel, and engaging the vessel marker with an inner wall of the vessel by deforming the vessel marker,
performing X-ray imaging on a living body region containing the vessel marker fixed in the vessel; and
performing notification of a radiation irradiation range based on a position of the imaged vessel marker.

Still other example aspect of the present invention provides a radiation irradiation control apparatus for controlling radiation irradiation by using the abovementioned vessel marker indwelled in a vessel of a patient, comprising:
a discriminator that irradiates a range including the vessel marker with an X-ray, and discriminates shapes of at least two indwelled vessel markers;
a calculator that calculates a tumor irradiation target position from positions of the at least two discriminated indwelled vessel markers; and
an irradiation controller that performs control to irradiate the tumor irradiation target position with therapeutic radiation having a selected intensity.

Still other example aspect of the present invention provides a vessel marker indwelling support apparatus for indwelling the abovementioned vessel marker in a vessel, comprising:
a storage that stores a tumor position, a vessel marker to be used, and at least two vessels in which the vessel marker is to be indwelled, in association with each other; and
a determinator that refers to the storage based on a tumor position as a target of radiotherapy, and determines a vessel marker to be used and at least two vessels in which the vessel marker is to be indwelled.

Advantageous Effects of Invention

According to the present invention, a more accurate radiotherapy can be performed.

BRIEF DESCRIPTION OF DRAWINGS

FIG. 1B is a view showing the shape of a vessel marker according to the first example embodiment of the present invention:

FIG. 2A is a flowchart showing the procedure of radiotherapy according to the second example embodiment of the present invention;

FIG. 4 is a block diagram showing the configuration of a vessel marker indwelling system according to the second example embodiment of the present invention, FIG. 5A is a flowchart showing the procedure of a radiotherapy preparation step according to the second example embodiment of the present invention;

FIG. 10 is a view showing the arrangement of a vessel selection database according to the third example embodiment of the present invention;

FIG. 13 is a view showing the arrangement of a tumor position tracking table according to the fourth example embodiment of the present invention.

DESCRIPTION OF EXAMPLE EMBODIMENTS

Example embodiments of the present invention will now be described in detail with reference to the drawings. It should be noted that the relative arrangement of the components, the numerical expressions and numerical values set forth in these example embodiments do not limit the scope of the present invention unless it is specifically stated otherwise. A term "vessel" in the example embodiments is a metabolism transport path of an organ or a tissue and includes the blood vessel system and the lymph system that are classified in accordance with the properties of a liquid flowing through the vessel.

First Example Embodiment

Figure 1A:
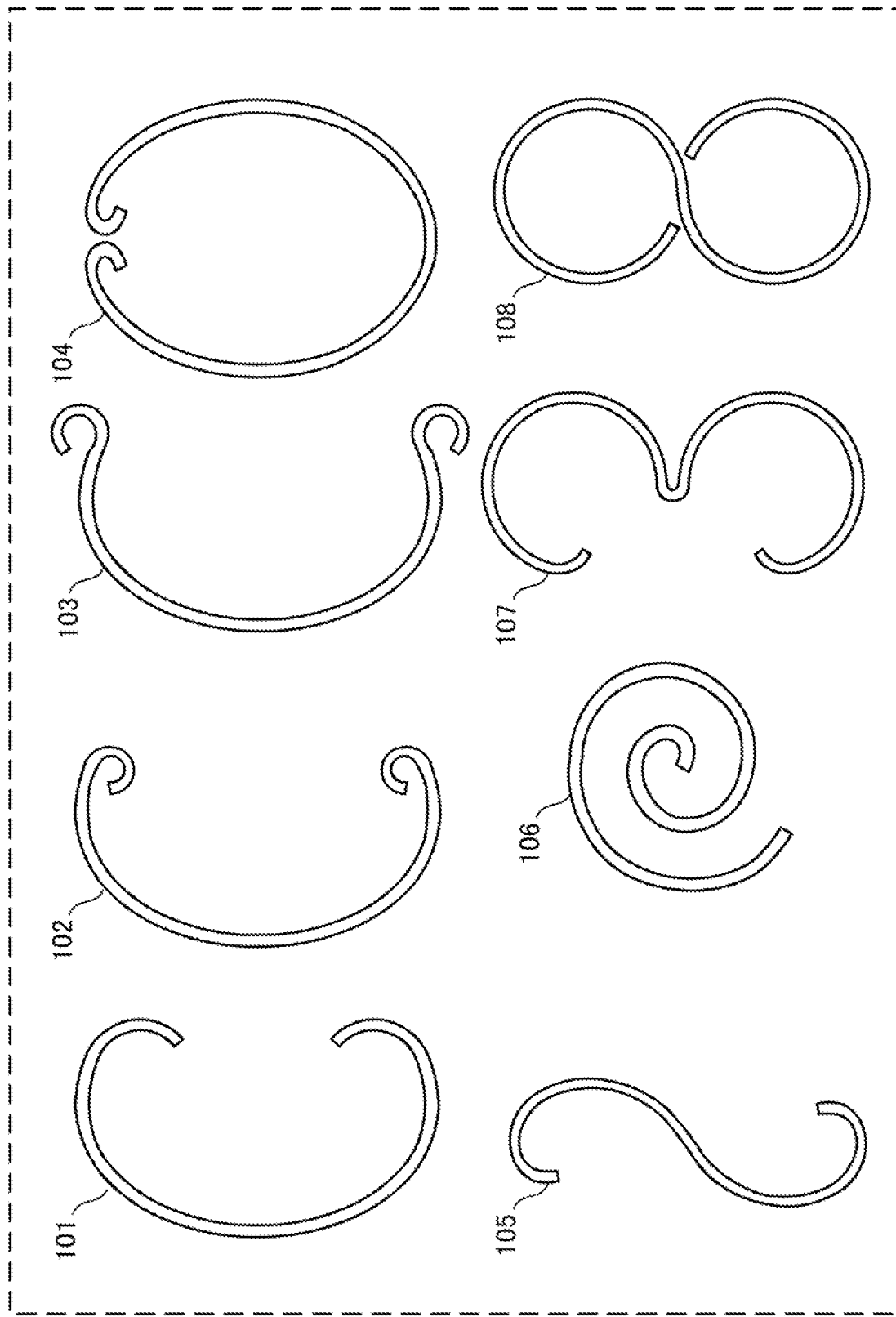
FIG. 1A is a view showing the shape of a vessel marker according to the first example embodiment of the present invention.

A vessel marker according to the first example embodiment of the present invention will be explained with reference to FIGS. 1A to 1E. Vessel markers 101 to 108 shown in FIG. 1A show deformed shapes when they are inserted into the vessel. The vessel markers 101 to 108 have two-dimensional curved shapes, and each shape includes a deformation fixed shape for engaging with the vessel inner wall, and a position notification shape for notifying the outside of a radiation irradiation position.

For example, when inserted into the vessel from inside a catheter, each of the vessel markers 101 to 103 is deformed from a linear shape to an almost C shape, and fixed in the vessel. The distal ends of the vessel marker 101 curve inward. The distal ends of the vessel marker 102 curl inward. The distal ends of the vessel marker 103 curl outward. On the other hand, when inserted into the vessel from inside a catheter, the vessel marker 104 is deformed from a linear shape to an almost O shape, and fixed in the vessel.

When inserted into the vessel from inside a catheter, the vessel marker 105 is deformed from a linear shape to an almost S shape, and fixed in the vessel. When inserted into the vessel from inside a catheter, the vessel marker 106 is deformed from a linear shape to a spiral shape, and fixed in the vessel.

Figure 3:
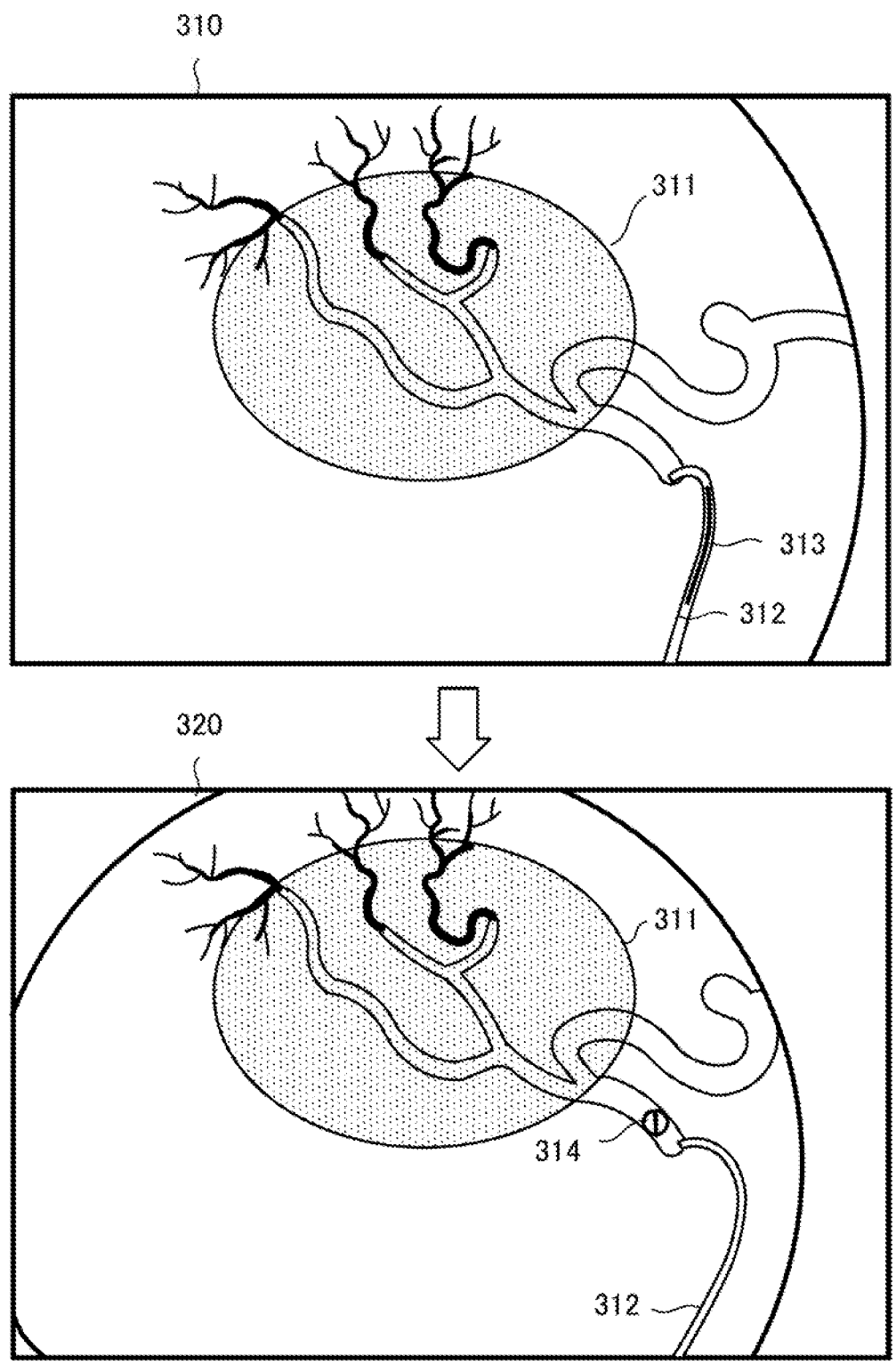
FIG. 3 is a view showing an outline of a vessel marker indwelling treatment according to the second example embodiment of the present invention.

When inserted into the vessel from inside a catheter, the vessel marker 107 is deformed from a linear shape to an almost figure 3 shape, and fixed in the vessel. When inserted into the vessel from inside a catheter, the vessel marker 108 is deformed from a linear shape to an almost figure 8 shape, and fixed in the vessel.

FIG. 1B is a view for explaining vessel markers 111 to 113 having three-dimensional curves. The vessel markers 111 to 113 shown in FIG. 1B show deformed shapes when they are inserted into the vessel. The vessel markers 111 to 113 have three-dimensional curved shapes, and each shape includes a deformation fixed shape for engaging with the vessel inner wall, and a position notification shape for notifying the outside of a radiation irradiation position.

The vessel marker 111 is indwelled in the vessel with a one-stroke three-dimensional curved shape obtained by connecting two arcs forming the surface of a sphere. The vessel marker 112 has a one-stroke three-dimensional curved shape obtained by connecting four half arcs forming the surface of a sphere and making the right angle with each other. The vessel marker 113 has a one-stroke three-dimensional curved shape obtained by connecting two half arcs making the right angle with one arc.

An image 114 is obtained by viewing the vessel marker 111 in the X direction, and has a shape in which the diameter is drawn in the center of a circle. An image 115 obtained by viewing the vessel marker 111 in the Y direction has a circular shape. An image 116 obtained by viewing the vessel marker 111 in the Z direction has a + (plus) shape. The X-ray fluoroscopic image of the vessel marker 111 indwelled in the vessel has a shape (a curved shape or a + shape) having a discriminable difference from a physiological or anatomical shape appearing in a living body in any direction, and includes a position notification shape for notifying the outside of a radiation irradiation position. Note that the vessel marker 111 has the three-dimensional curved shape in which two circles intersect each other at an almost right angle, but the intersecting angle is not limited to the right angle. The X-ray fluoroscopic image of each of the vessel markers 112 and 113 also has a shape similar to the images 114 to 116, and includes a position notification shape for notifying the outside of a radiation irradiation position. That is, the vessel markers 111 to 113 are small and implement both recognizability from the outside and fixability in the vessel. The position notification shape need only include a shape that makes a recognition point conspicuous. Examples are the intersection of straight lines, and the intersection of a circle and a straight line.

Figure 1C:
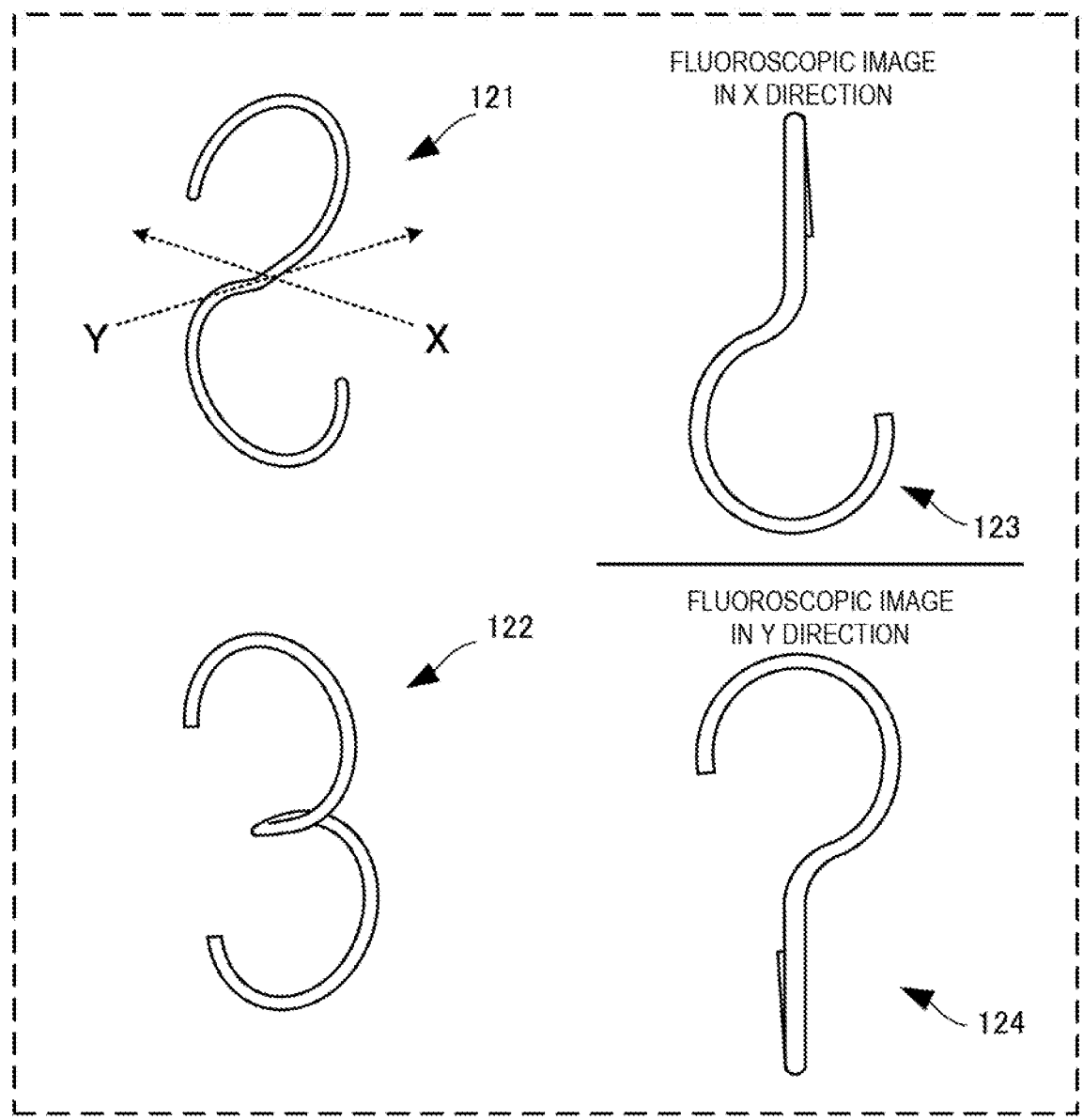
FIG. 1C is a view showing the shape of a vessel marker according to the first example embodiment of the present invention.

FIG. 1C is a view for explaining vessel markers 121 and 122 having three-dimensional curves. The vessel markers 121 and 122 show deformed shapes when they are inserted into the vessel. The vessel markers 121 and 122 have three-dimensional curved shapes, and each shape includes a deformation fixed shape for engaging with the vessel inner wall, and a position notification shape for notifying the outside of a radiation irradiation position.

Each of the vessel markers 121 and 122 has a twisted S shape in which the upper curve and the lower curve of the S shape are twisted. An image 123 or 124 obtained by viewing the vessel marker 121 in the X or Y direction has a two-dimensional curved shape having a discriminable difference from a living tissue. Note that the vessel marker 121 has the three-dimensional curved shape in which the upper formation surface and the lower formation surface of the S shape are twisted at an almost right angle. However, the twisting angle is not limited to the right angle, and can also be any angle as long as a characteristic fluoroscopic image can be obtained in any direction. Note also that the X- and Y-direction fluoroscopic images are taken as typical examples, but a fluoroscopic image in another direction has a two-dimensional curved shape having a discriminable difference from a living tissue.

A marker 122 has a similar shape in which the upper formation surface and the lower formation surface of the S shape are twisted, but has a three-dimensional curved shape in which the twisting direction is different from that of the vessel marker 121. X-ray fluoroscopic images of the vessel marker 125 are similar to the images 123 and 124.

Figure 1D:
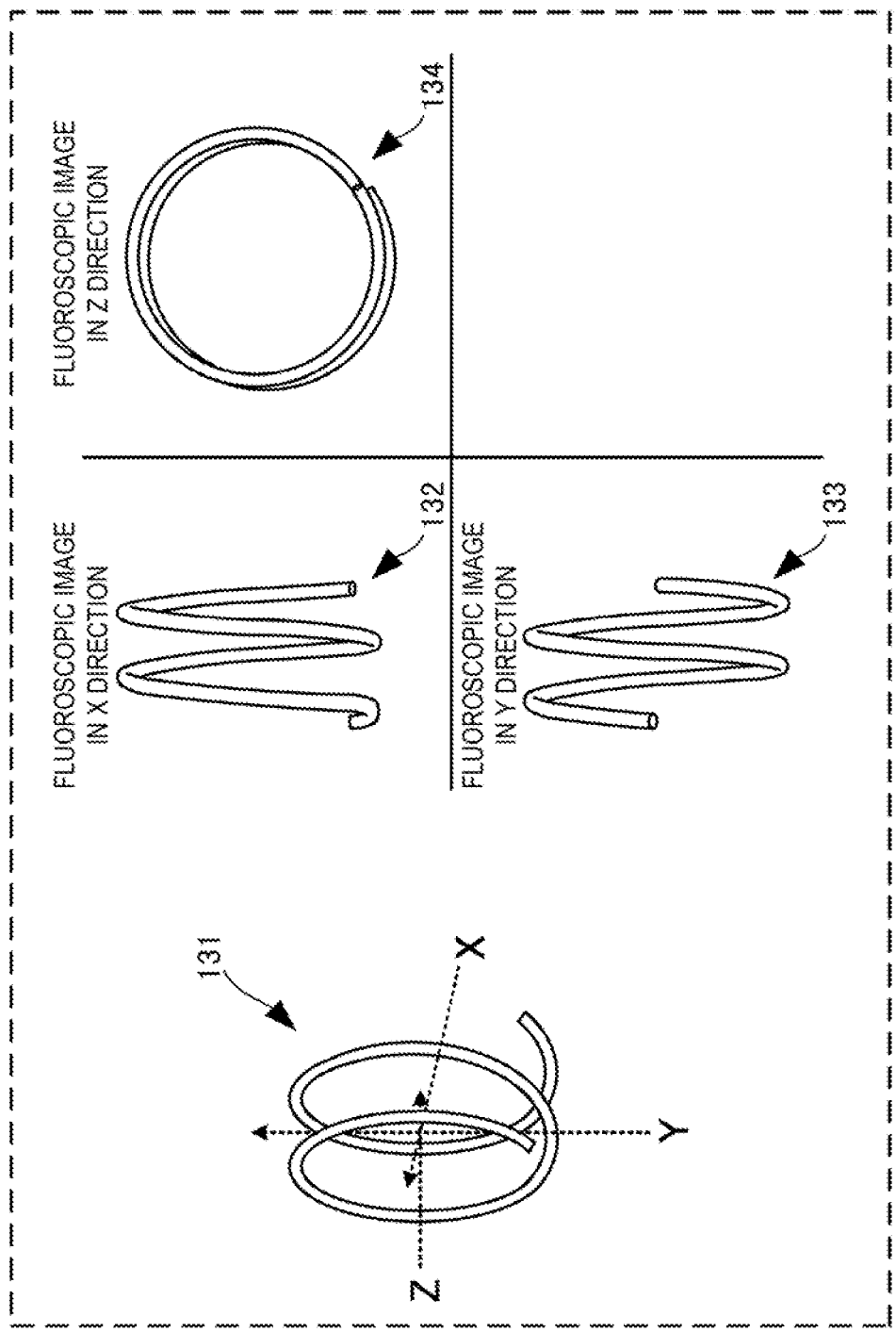
FIG. 1D is a view showing the shape of a vessel marker according to the first example embodiment of the present invention.

FIG. 1D is a view for explaining a vessel marker 131 having a three-dimensional curve. The vessel marker 131 shows a deformed shape when it is inserted into the vessel. The vessel marker 131 has a three-dimensional curved shape, and the shape includes a deformation fixed shape for engaging with the vessel inner wall, and a position notification shape for notifying the outside of a radiation irradiation position.

The vessel marker 131 has a double circular coil shape having equal diameters. Fluoroscopic images 132 to 134 obtained by viewing the vessel marker 131 in the X, Y, and Z directions have shapes having discriminable differences from a living tissue, and can notify the outside of a radiation irradiation position. Note that the vessel marker 131 has the double spring shape having equal diameters, but the diameters need not be equal. The spring shape is not limited to a double spring shape, but is preferably a short spring shape.

Figure 1E:
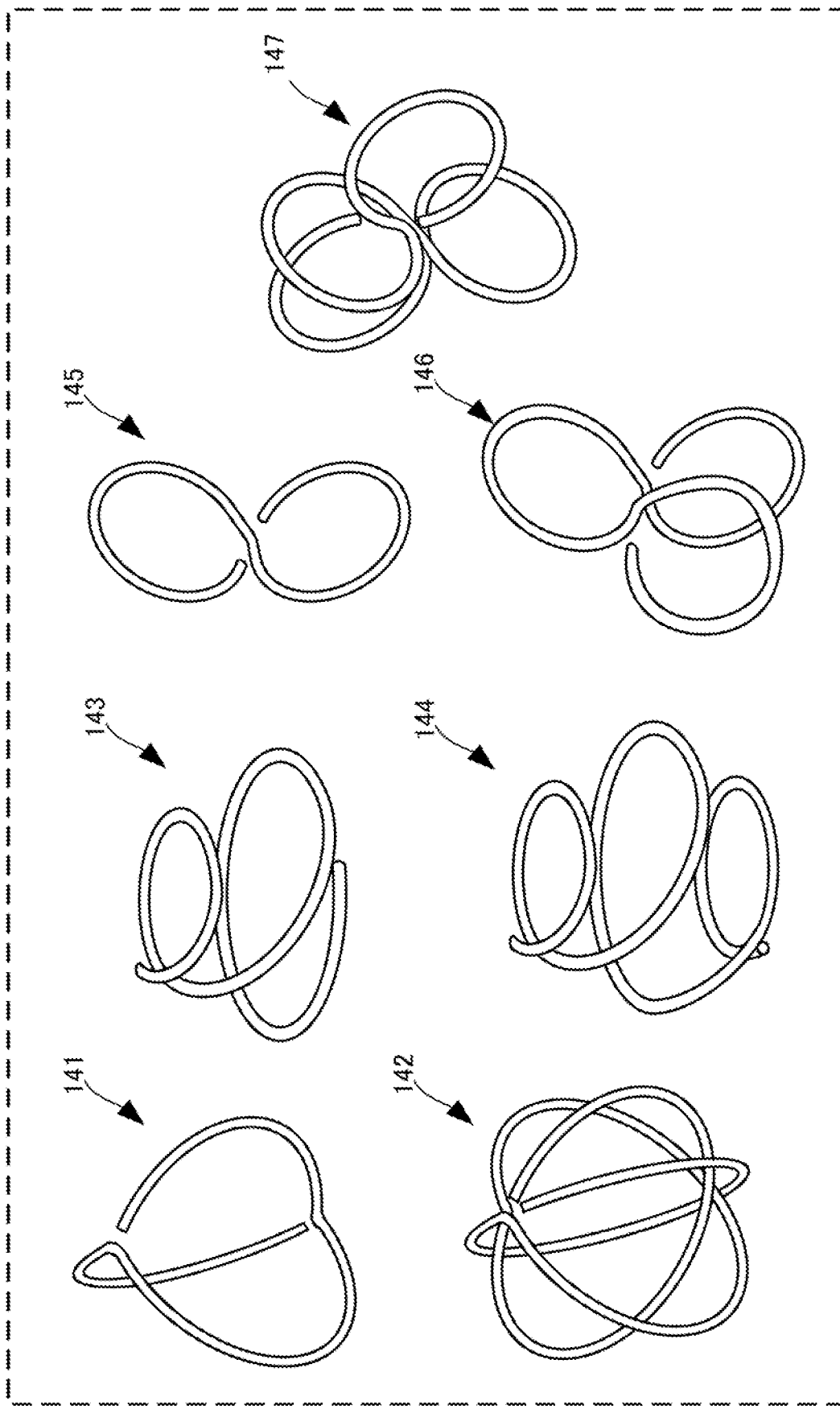
FIG. 1E is a view showing the shape of a vessel marker according to the first example embodiment of the present invention.

FIG. 1E is a view showing other vessel marker examples. Vessel markers 141 to 145 also have three-dimensional curved shapes, and each shape includes a deformation fixed shape for engaging with the vessel inner wall, and a position notification shape for notifying the outside of a radiation irradiation position.

The vessel marker 141 has a shape obtained by connecting three half arcs at an angle of about 120°. The vessel marker 142 has a shape obtained by connecting six half arcs at an angle of 60°. In other words, three circles intersect each other and form an almost spherical shape as a whole.

The vessel marker 143 has a double spring shape having different diameters, and the vessel marker 144 has a triple spring shape in which the diameter changes like small→large→small. A triple spring shape in which the diameter changes like large→small→large is also possible. When the vessel marker has a spring-like three-dimensional curved shape having different diameters, a small-diameter portion does not collapse but forms a beautiful circle even when the inner diameter of the vessel is smaller than the large diameter of the spring-like vessel marker.

Figure 8:
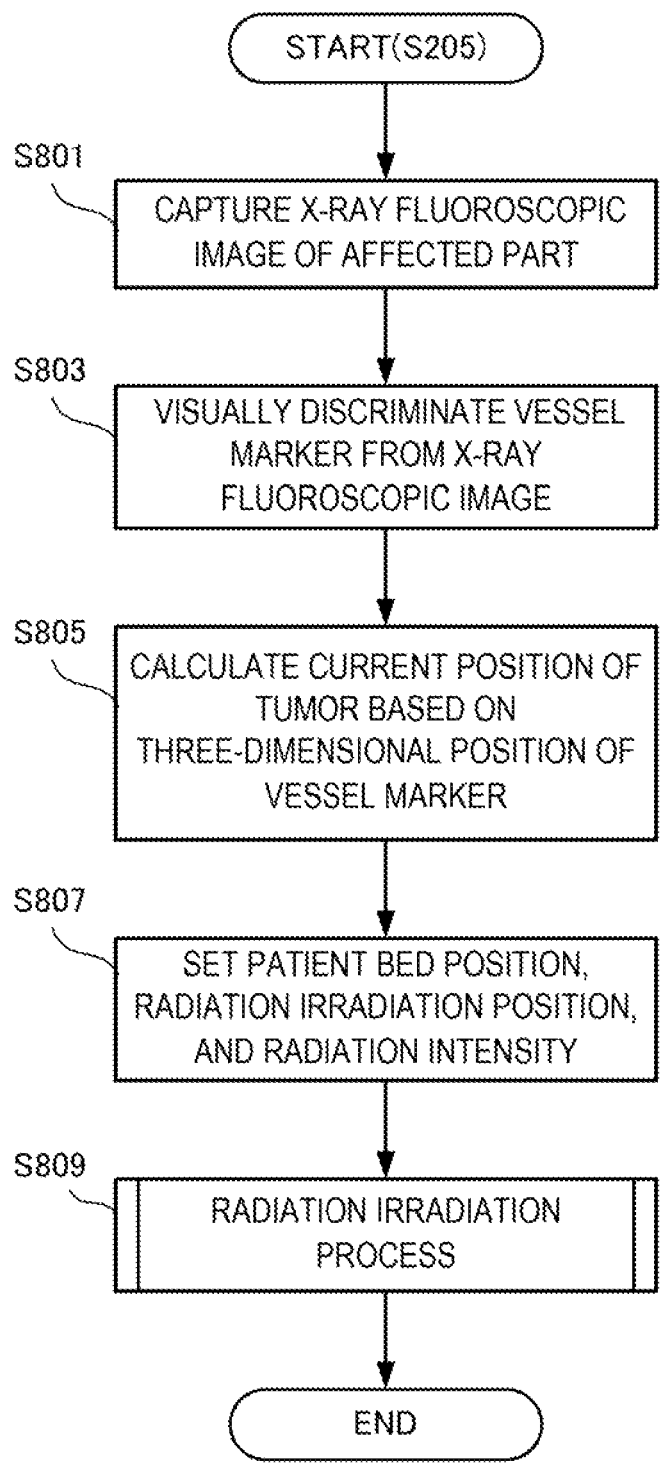
FIG. 8 is a flowchart showing the procedure of a radiotherapy execution step according to the second example embodiment of the present invention.

The vessel marker 145 has a twisted FIG. 8 shape in which the upper curve and the lower curve are twisted. Like the vessel markers 121 and 122 shown in FIG. 1B, the vessel marker 145 has a characteristic fluoroscopic image in any direction, and has a shape having a discriminable difference from a living tissue. A vessel marker 146 has a shape obtained by connecting three arcs, instead of half arcs. It is, of course, also possible to connect four or more arcs. A vessel marker 147 has a shape in which two FIG. 8 shapes in twisted positions are connected in the center.

In this example embodiment, the vessel markers 111 to 113, 141, and 142 will be referred to as spherical curved shapes. Also, the vessel markers 131, 143, and 144 will be referred to as spring shapes having equal diameters or different diameters.

Each of the vessel markers 101 to 147 deforms itself into a shape having a discriminable difference from a living tissue. The minor diameter is desirably 1 to 5 mm in accordance with the diameter of the vessel in a human body. The major diameter is desirably about 5 mm. The diameter of a wire material for forming the vessel markers was 0.508 to 0.559 mm (0.020 to 0.022 inches), but the diameter is not limited to this. A therapeutic radiation is any of a proton beam, a heavy particle beam, an X-ray, and an electron beam. The vessel marker is desirably manufactured by using a spring material or a shape memory material that does not cause any allergic reaction in a human body, does not change with time, is depicted by an X-ray fluoroscopic image, is also depicted by MRI (Magnetic Resonance Imaging) as needed, and absorbs radiation. An example is a platinum-containing metal. The vessel marker is desirably formed by using a nonmagnetic material that reduces metal artifact. Since the purpose of the marker is not embolism, a shape and a material (non-embolismic material) that hardly cause embolism are used. That is, it is desirable to avoid a platinum coil, gelatin sponge, and plastic particle. In particular, the marker is preferably not long (10 mm or less) in the longitudinal direction.

Note that the shape of the vessel marker is not limited to the shapes shown in FIGS. 1A to 1E. That is, it is possible to use any shape including a shape discriminable from a physiological or anatomical shape appearing in a living body. Also, the shape need only have a diameter with which the vessel marker can be deformed and indwelled in a target vessel, and need only be a shape with which the vessel marker does not damage the inner surface of the vessel. That is, if the vessel marker is too small, the marker cannot be fixed in an arbitrary position in the vessel. If the vessel marker is too large, the marker cannot form a target shape in the vessel and may damage the inner surface of the vessel. Therefore, the vessel marker is desirably deformable to a size matching the diameter of the vessel. Furthermore, it is necessary to minimize the appearance of metal artifact in a CT image that is essential when executing a radiotherapy plan. Accordingly, it is desirable to use a shape by which no wire material exists in the vessel, and restrict the mass of the vessel marker.

In this example embodiment, after the vessel marker having a linear shape is inserted into the vessel, the vessel marker deforms itself into a curved shape and stays in the vessel. Therefore, the marker indwelling portion is not limited unlike conventional percutaneous needling. By using the indwelled vessel marker as a mark for determining a radiation irradiation range, an accurate radiotherapy that does not cause many complications can be implemented.

This example embodiment has the following merits compared to the conventional method (percutaneous indwelling).

(1) The vessel is a tube through which a body fluid flows in a living body, and includes the blood vessel and the lymph vessel. Since the vessels exist in a whole body, indwelling portions are not largely limited.

(2) Theoretically, a portion that can cause bleeding is limited to a catheter insertion portion, and manual astriction can easily be performed on this portion. This makes safer indwelling possible.

(3) A tumor tissue is not physically damaged, and this eliminates the risk that causes iatrogenic tumor metastasis such as peritoneal dissemination or pleural dissemination.

This example embodiment can implement a vessel marker that hardly embolizes the blood vessel, hardly causes metal artifact, and can easily be recognized in various directions. This makes it possible to more accurately irradiate a tumor with radiation.

When embolism is the purpose, a linear coil is used for a thin blood vessel, and a long-spring-like coil is used for a thick blood vessel. However, these shapes are selected in order to assure a high embolizing power.

The purpose of this example embodiment is not embolism but a method of balancing an in-blood-vessel fixing function and an external discriminating function at high level. For this purpose, it is desirable to use a shape that is caught on the inner surface of the blood vessel by an elastic force, is easily discriminated from a physiological or anatomical shape appearing in a living body, is conspicuous when viewed in various directions, and does not cause much metal artifact (it is desirable to use a short nonmagnetic body having a small mass).

Second Example Embodiment

A radiotherapy system according to the second example embodiment of the present invention will be explained below. In the radiotherapy system according to this example embodiment, a vessel marker as explained in the first embodiment is fixed in the vessel in order to specify the position of a tumor regardless of relative position movement of the tumor caused by external factors such as body motion, and internal factors such as breathing, a heartbeat, gastrointestinal peristalsis, and physiological movement, expansion, and reduction of organs. Then, the indwelled vessel marker is imaged by X-ray fluoroscopy, and the range and shape of radiation irradiation are determined. This minimizes radiation irradiation to normal tissues other than the tumor.

<<Procedure of Radiotherapy>>

FIG. 2A is a flowchart showing the procedure of radiotherapy according to this example embodiment.

Figure 2B:
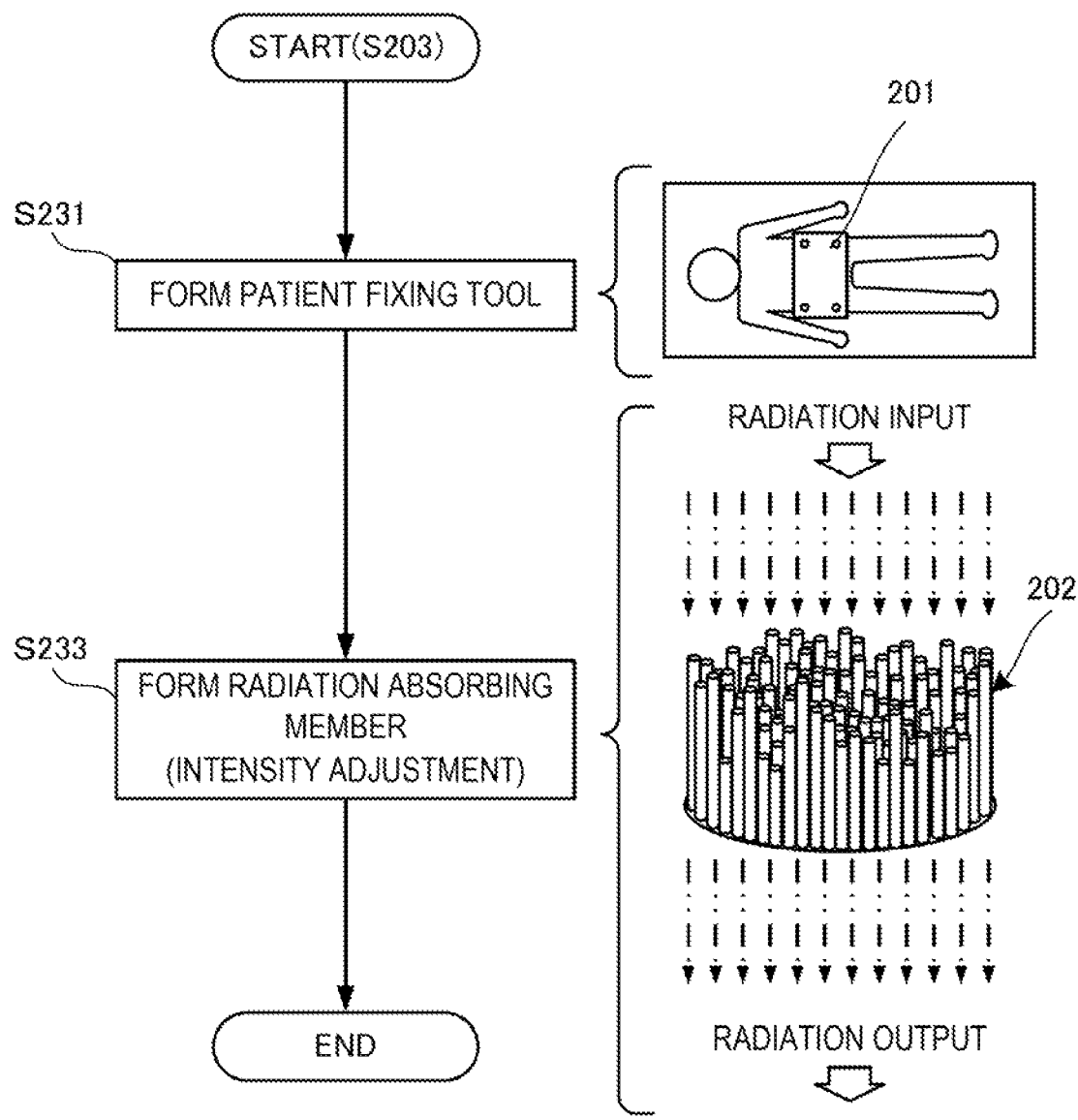
FIG. 2B is a flowchart showing the procedure of a radiotherapy planning step (S203) according to the second example embodiment of the present invention.

When performing radiotherapy, a radiation irradiation preparation step is performed in step S201. In this radiotherapy preparation step, an X-ray fluoroscopic apparatus of a patient is used to determine the position and shape (range) of a tumor based on an angiographic image obtained by injecting a contrast agent. Then, the type of vessel marker is selected based on the positional relationship between a selectable vessel and the tumor, a vessel in which the vessel marker is to be indwelled and the indwelling position are decided, and a treatment of indwelling the selected vessel marker is performed. In step S203, a radiotherapy plan is constructed. FIG. 2B is a flowchart showing details of processing in a radiotherapy planning step (S203). In step S231, a resin fixing tool 201 (for fixing a body on a therapy table) is formed in accordance with the shape of the body of the patient. The formed resin fixing tool 201 is used whenever radiation irradiation is performed. Then, in step S233, a radiation absorbing member 202 for matching the in-body depth, to which radiation reaches, with the tumor range by adjusting the radiation intensity is formed.

The relative positions of the body surface, the tumor, and the vessel marker are three-dimensionally measured by capturing a CT image with the resin fixing tool 201 being attached. Then, the range of the tumor is depicted in the CT image, and simulation of how to emit radiation is performed. A synthetic image of an MRI image or a PET image is used in some cases in order to depict the position of the tumor as accurately as possible. After that, the number, directions, intensities, and divided doses of radiation beams for irradiating the tumor with the target radiation dose are determined while minimizing the radiation exposure dose to the risk organ.

Also, the radiation absorbing member 202 is formed in order to adjust a uniform radiation from a radiation accelerator in accordance with the depth of the tumor in the body. To obtain a radiation intensity corresponding to the range and depth of the tumor extracted from the CT image, the radiation absorbing member 202 is formed by using, for example, a 3D printer so that the corresponding length of the radiation absorbing material is obtained.

By referring to FIG. 2A again, a radiotherapy execution step is performed in step S205. That is, the patient, particularly, the affected part of the patient is fixed on the therapy table of a radiotherapy room by the fixing tool. Then, the vessel marker is discriminated from an X-ray fluoroscopic image or a CT image, and the position of the tumor is decided from the three-dimensional position of the vessel marker. The patient bed or the irradiator is moved to match the decided tumor position with the simulated tumor position. Subsequently, the tumor is irradiated with radiation such as an X-ray, an electron beam, a proton beam, or a heavy particle beam. This radiation irradiation is performed based on the radiation dose planned in the radiotherapy planning step.

<<Vessel Marker Indwelling>>

The vessel marker indwelling process in the radiotherapy preparation step (S201) will be explained in detail below.

(Outline)

FIG. 3 is a view showing an outline of the vessel marker indwelling treatment. A treatment of indwelling the vessel marker in the artery near the tumor will be explained below.

In this vessel marker indwelling treatment, a sheath is inserted into the femoral artery of the patient from the right inguinal region, and a guiding catheter is inserted into the major artery of the target organ through the sheath. Then, a microcatheter having a smaller diameter is inserted into the guiding catheter.

The microcatheter is inserted into a preselected indwelling target position of the vessel marker, and the vessel marker is pushed into the artery through the microcatheter, thereby indwelling the vessel marker deformed into a predetermined shape in the artery. Whether the vessel marker is indwelled in a position effective for the radiotherapy is confirmed by capturing a CT image. If no effectiveness can be expected, an additional vessel marker is indwelled as needed. It is desirable to indwell two or more vessel markers. If it is determined that the vessel marker is indwelled in the expected position, the catheters and the sheath are removed, and bleeding is stopped.

Note that in order to increase the tumor position calculation accuracy, it is also possible to confirm the movement of the position by capturing CT images on the next day and the day after next. In addition, the catheter can also be inserted from the artery of the upper arm or the forearm, or from the vein of the inguinal region.

An angiographic image 310 of the vessel marker indwelling treatment shown in FIG. 3 shows a state in which a microcatheter 312 is inserted into the position of an artery where a tumor position 311 can be decided, and a selected linear vessel marker 313 is inserted into the microcatheter 312.

An angiographic image 320 of the vessel marker indwelling treatment shown in FIG. 3 shows a state in which the linear vessel marker 313 inserted through the microcatheter 312 is pushed into the artery, and indwelled as it is deformed into an S-shaped vessel marker 314.

Note that FIG. 3 shows indwelling of one S-shaped vessel marker 314, but the number of vessel markers to be indwelled is determined so that the tumor position can be calculated and decided. Vessel markers to be indwelled can have the same shape, but it is desirable to use vessel markers having different shapes so that each marker can be specified.

(Vessel Marker Indwelling System)

FIG. 4 is a block diagram showing the configuration of a vessel marker indwelling system 400.

The vessel marker indwelling system 400 includes an X-ray fluoroscopic imager 415 capable of depicting an angiographic image by an X-ray fluoroscopic image, a treatment room 410 for indwelling a vessel marker, and a vessel marker indwelling support apparatus 420 for supporting indwelling of the vessel marker.

In the treatment room 410, a patient 412 exists on a treatment table 411, and a doctor 413 for performing a vessel marker indwelling treatment also exists. The treatment room 410 includes a display 414 for displaying an angiographic image, and the X-ray fluoroscopic imager 415. The doctor 413 performs the vessel marker indwelling treatment as shown in FIG. 3, while observing an angiographic image on the display 414.

The vessel marker indwelling support apparatus 420 includes a tumor position and vessel display controller 421, a display 422, a vessel marker position input unit 423, a vessel marker indwelling evaluator 424, and an indwelling evaluation database 425. The tumor position and vessel display controller 421 controls the display of a tumor position in an image from the X-ray fluoroscopic imager 415, on the displays 414 and 422. The vessel marker position input unit 423 inputs the position of the indwelled vessel marker. The vessel marker indwelling evaluator 424 evaluates whether the tumor position can be calculated and decided from the input vessel marker indwelling position. The indwelling evaluation database 425 stores data to be used in evaluation by the vessel marker indwelling evaluator 424. If the vessel marker indwelling evaluator 424 evaluates that it is impossible to calculate and decide the tumor position from the vessel marker indwelling position, the vessel marker indwelling evaluator 424 notifies the doctor 413 that it is necessary to further indwell a vessel marker. Note that the processing performed by the vessel marker position input unit 423, the vessel marker indwelling evaluator 424, and the indwelling evaluation database 425 may also be performed by the doctor as indicated by the broken lines.

(Vessel Marker Indwelling Procedure)

FIG. 5A is a flowchart showing a detailed procedure of the radiotherapy preparation step (S201).

In the radiotherapy preparation step (S201), an angiographic image of the affected part of the patient is acquired in step S511. Then, in step S513, a tumor position is specified from the angiographic image. Subsequently, a vessel marker to be used and the indwelling position of the vessel marker are selected based on the tumor position. In relation to the tumor position, an appropriate artery linked with the tumor position is selected in accordance with, for example, breathing, a heartbeat, gastrointestinal peristalsis, and a change in form of an organ. As the vessel marker indwelling position, it is also possible to select an artery outside a target organ, which is close to the organ and allows easy indwelling.

In step S17, a vessel marker indwelling process is performed based on the selected vessel marker and vessel marker indwelling position.

Figure 5B:
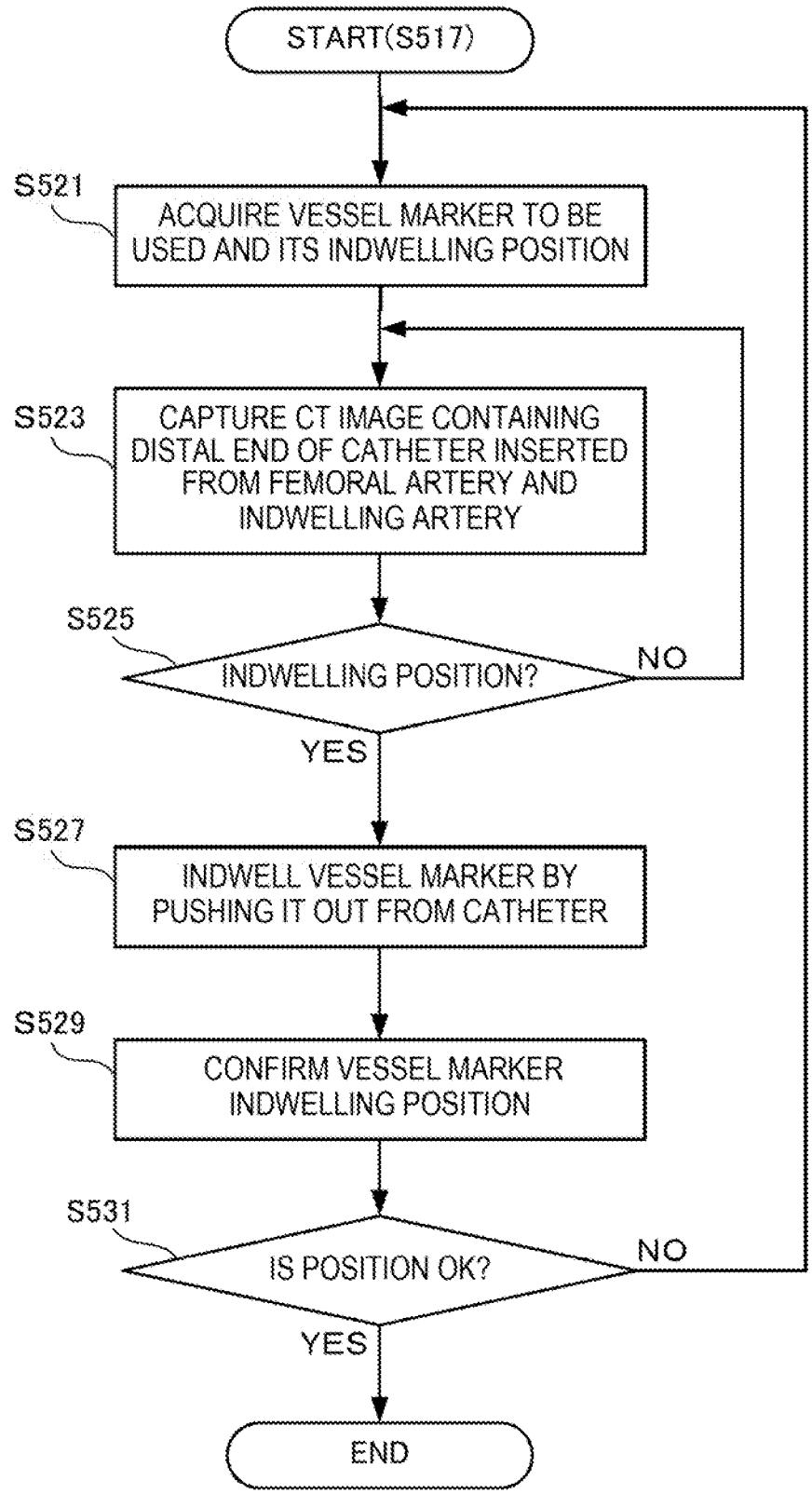
FIG. 5B is a flowchart showing the procedure of a vessel marker indwelling process according to the second example embodiment of the present invention.

FIG. 5B is a flowchart showing the procedure of the vessel marker indwelling process (S517).

In the vessel marker indwelling process (S517), a vessel marker to be used and a vessel marker indwelling position are set in step S521. By repeating steps S523 and S525, the distal end of a microcatheter inserted from the femoral artery is allowed to reach the vessel marker indwelling position while capturing an angiographic image including the distal end of the microcatheter and the artery in which the vessel marker is to be indwelled. If the distal end of the microcatheter cannot reach the vessel marker indwelling position, for example, if the tumor has extended to the artery, the vessel marker indwelling position is changed to another artery.

If the distal end of the microcatheter has reached the vessel marker indwelling position, the process advances to step S527, and the selected linear vessel marker is pushed out from the microcatheter. The pushed linear vessel marker is deformed into a predetermined shape discriminable from the human body tissue, caught inside the vessel, and indwelled.

When the vessel marker is indwelled, the process advances to step S529, and whether the vessel marker is indwelled in a position effective for radiotherapy is confirmed by capturing a CT image or the like. If the position of the vessel marker is incorrect, that is, if the tumor position cannot be calculated, the process is repeated from step S521 in order to indwell the vessel marker again.

<<Radiotherapy Planning>>

The radiotherapy planning step (S203) has been explained in detail in the explanation of FIG. 2, so a repetitive explanation will be omitted.

Note that in radiotherapy, a target total dose is divisionally radiated over a plurality of times or a plurality of days by taking account of the safety. For example, a lung cancer is divisionally irradiated four times in some cases, and divisional irradiation like this makes it possible to perform a safe radiotherapy using the difference between the recovery factor of a normal tissue and that of a tumor tissue. Multi-divisional (long-term) irradiation is often performed if an organ having a high radiosensitivity such as the alimentary canal is adjacent to the affected part.

<<Radiotherapy Using Vessel Marker>>

(Outline)

Figure 6:
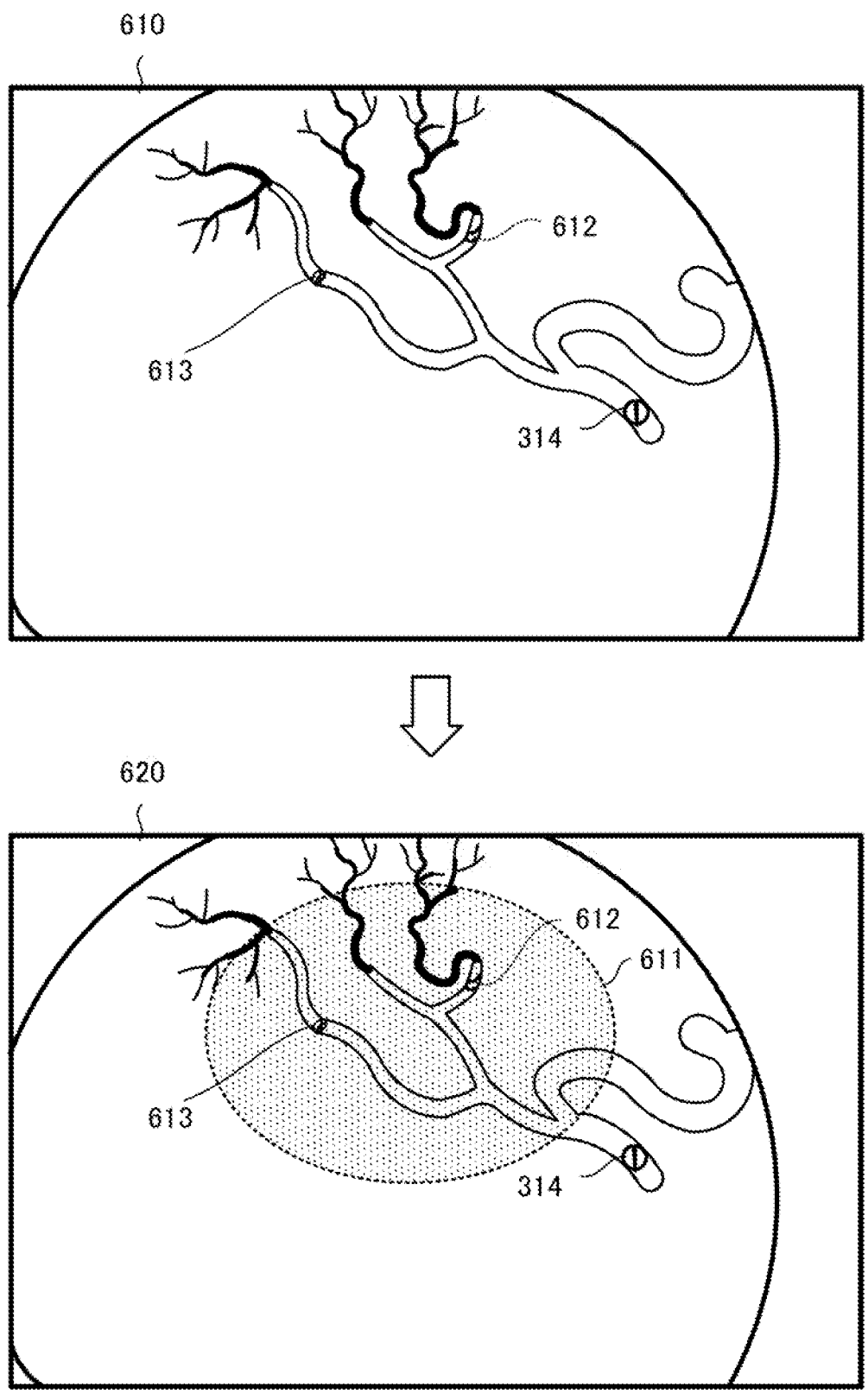
FIG. 6 is a view showing an outline of radiation irradiation using a vessel marker according to the second example embodiment of the present invention.

FIG. 6 is a view showing an outline of radiation irradiation using the vessel marker.

Radiotherapy is performed based on the established radiotherapy plan. In this radiotherapy, the patient is fixed on the therapy table by using the fixing tool. Then, the vessel marker is identified from an X-ray fluoroscopic image obtained by an X-ray fluoroscopic apparatus. Tumor position variation amounts (three axes including X, Y, and Z. or six axes including the rotations of the three axes) from the initially set position are calculated from the position of the identified vessel marker, the therapy table or the irradiator is moved, and radiation corresponding to the radiotherapy plan is emitted. Especially when the target is an abdominal tumor such as a lung cancer, a liver cancer, a bile duct cancer, or a pancreatic cancer, the relative position of the tumor largely varies in the body, so positioning is important.

An X-ray fluoroscopic image 610 during the radiation irradiation process shown in FIG. 6 is an image containing three vessel markers 314, 612, and 613. As shown in FIG. 6, the vessel marker 314 has an S shape, the vessel marker 612 has an O shape, and the vessel marker 613 has a double circle shape, that is, each vessel marker has a shape having a discriminable difference from a physiological or anatomical shape appearing in a living body, so the marker can easily be discriminated as a shape that does not exist in the human tissue. FIG. 6 shows the three vessel markers 314, 612, and 613, but it is also possible to use two vessel markers (the second one is a backup) as long as the markers can be indwelled in appropriate positions. On the other hand, three or more vessel markers can be indwelled if appropriate dwelling is difficult. To precisely align the marker position of CT captured many days ago with the marker position of the patient to be irradiated, it is ideal to use six axes (translations in the X, Y, and Z directions+rotations in the X, Y, and Z directions), but three axes (translations in the X, Y, and Z directions) are also usable.

In an X-ray fluoroscopic image 620 during the radiation irradiation process shown in FIG. 6, radiation is emitted to a tumor position 611 calculated and decided from the three vessel markers 314, 612, and 613, or the two markers 314 and 612. Note that the tumor position 611 is three-dimensional, so irradiation is performed by changing the irradiation intensity in accordance with the range of depth. For example, the irradiation intensity is changed by the function of the radiation absorbing member 202.

(Radiotherapy System)

Figure 7:
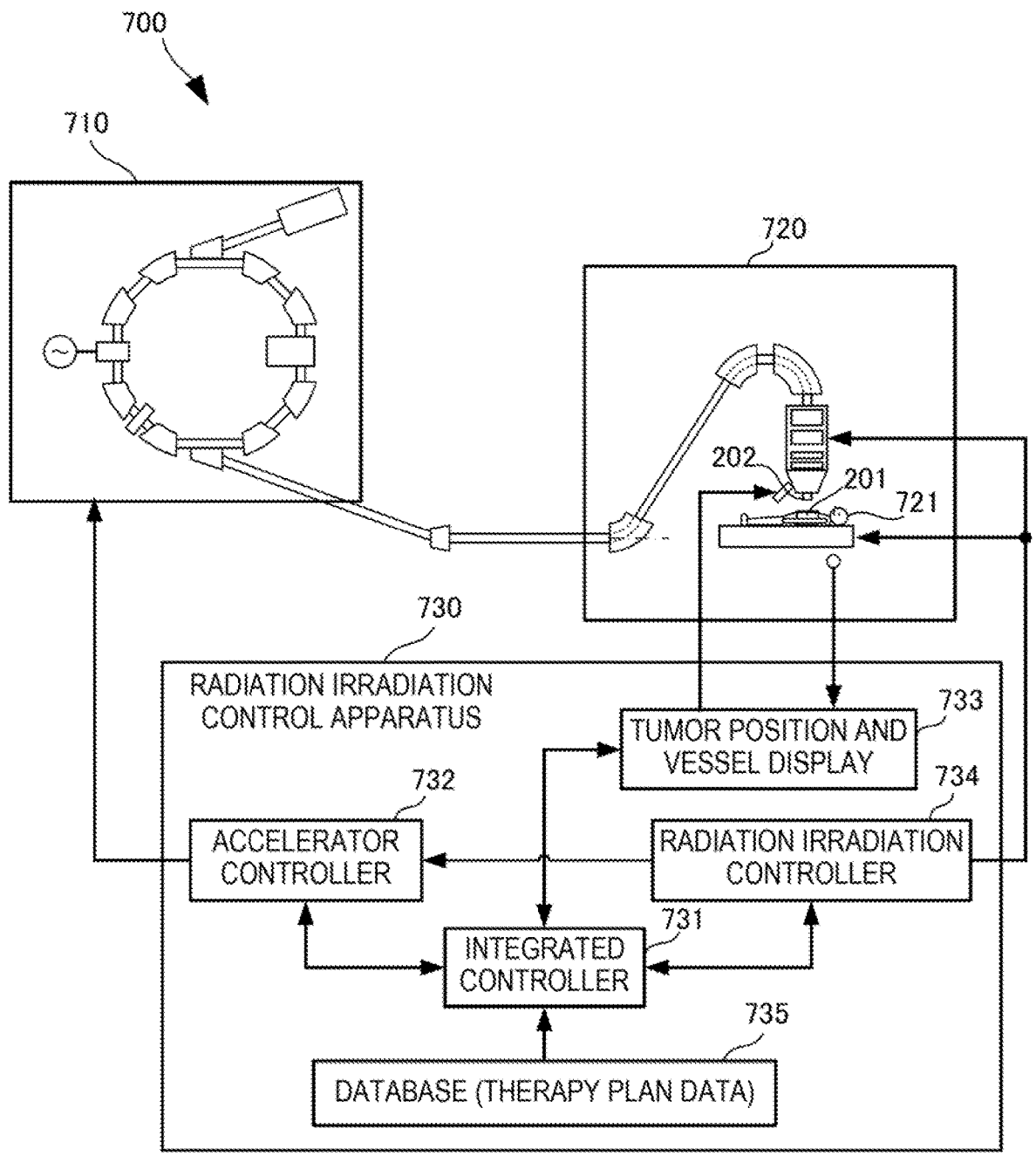
FIG. 7 is a block diagram showing the configuration of a radiation irradiation system using a vessel marker according to the second example embodiment of the present invention.

FIG. 7 is a block diagram showing the configuration of a radiation irradiation system 700 using the vessel marker.

The radiation irradiation system 700 includes an accelerator 710, a radiotherapy room 720, and a radiation irradiation control apparatus 730.

The radiotherapy room 720 includes an X-ray fluoroscopic apparatus, and irradiates a patient 721 fixed on the therapy table by the resin fixing tool 201 with radiation such as a proton beam or a heavy particle beam under the control of the radiation irradiation control apparatus 730, while adjusting the intensity of the radiation by the radiation absorbing member 202.

The radiation irradiation control apparatus 730 includes an integrated controller 731, an accelerator controller 732, a tumor position and vessel display 733, a radiation irradiation controller 734, and a database 735. The integrated controller 731 refers to radiotherapy plan data stored in the database 735, and controls individual function constituent parts by associating them with each other. The accelerator controller 732 controls the accelerator 710 to generate radiation such as a proton beam or a heavy particle beam, after preparations of radiation irradiation to the patient 721 in the radiotherapy room 720 are complete. The tumor position and vessel display 733 displays an image including a vessel marker of an X-ray fluoroscopic image captured by the X-ray fluoroscopic apparatus in the radiotherapy room 720.

The radiation irradiation controller 734 calculates an irradiation range (=tumor position) from the position of the vessel marker input based on discrimination of the vessel marker displayed on the tumor position and vessel display 733, and controls the position and intensity of radiation irradiation. Note that the radiation irradiation position is adjusted by moving or rotating the patient bed. The database 735 stores the radiotherapy plan data.

(Procedure of Radiotherapy)

FIG. 8 is a flowchart showing the procedure of the radiotherapy execution step (S205).

In the radiotherapy execution step (S205), an X-ray fluoroscopic image of the affected pan of the patient is captured in step S801. In step S803, a vessel marker is discriminated from the X-ray fluoroscopic image. In step S805, the current position of the tumor is calculated based on the three-dimensional position of the vessel marker. In step S807, the patient bed position, the irradiation position, and the irradiation intensity are set with respect to the current position of the tumor. Then, an irradiation process is performed in step S809.

In this example embodiment, a vessel marker having a specific shape is indwelled in the vessel, and, even when physiological movements of an organ and a tumor such as breathing, a heartbeat, and peristalsis occur, it is possible to recognize an accurate tumor position based on the vessel marker and irradiate the tumor with radiation. Accordingly, the marker indwelling position is not limited, the load on the patient is reduced, and radiotherapy that suppresses the development of complications can be performed. That is, a metal marker can be indwelled more safely for a tumor in an organ or a region in which indwelling cannot be performed by the conventional methods.

Third Example Embodiment

A vessel marker indwelling support apparatus according to the third example embodiment of the present invention will be explained below. The vessel marker indwelling support apparatus according to this example embodiment differs from the abovementioned second example embodiment in that the apparatus includes an arrangement for performing notification of an appropriate vessel marker indwelling place from tumor information. The rest of the arrangement and the operation are the same as the second example embodiment, so the same reference numerals denote the same arrangement and the same operation, and a detailed explanation thereof will be omitted.

<<Arrangement of Vessel Marker Indwelling Support Apparatus>>

Figure 9:
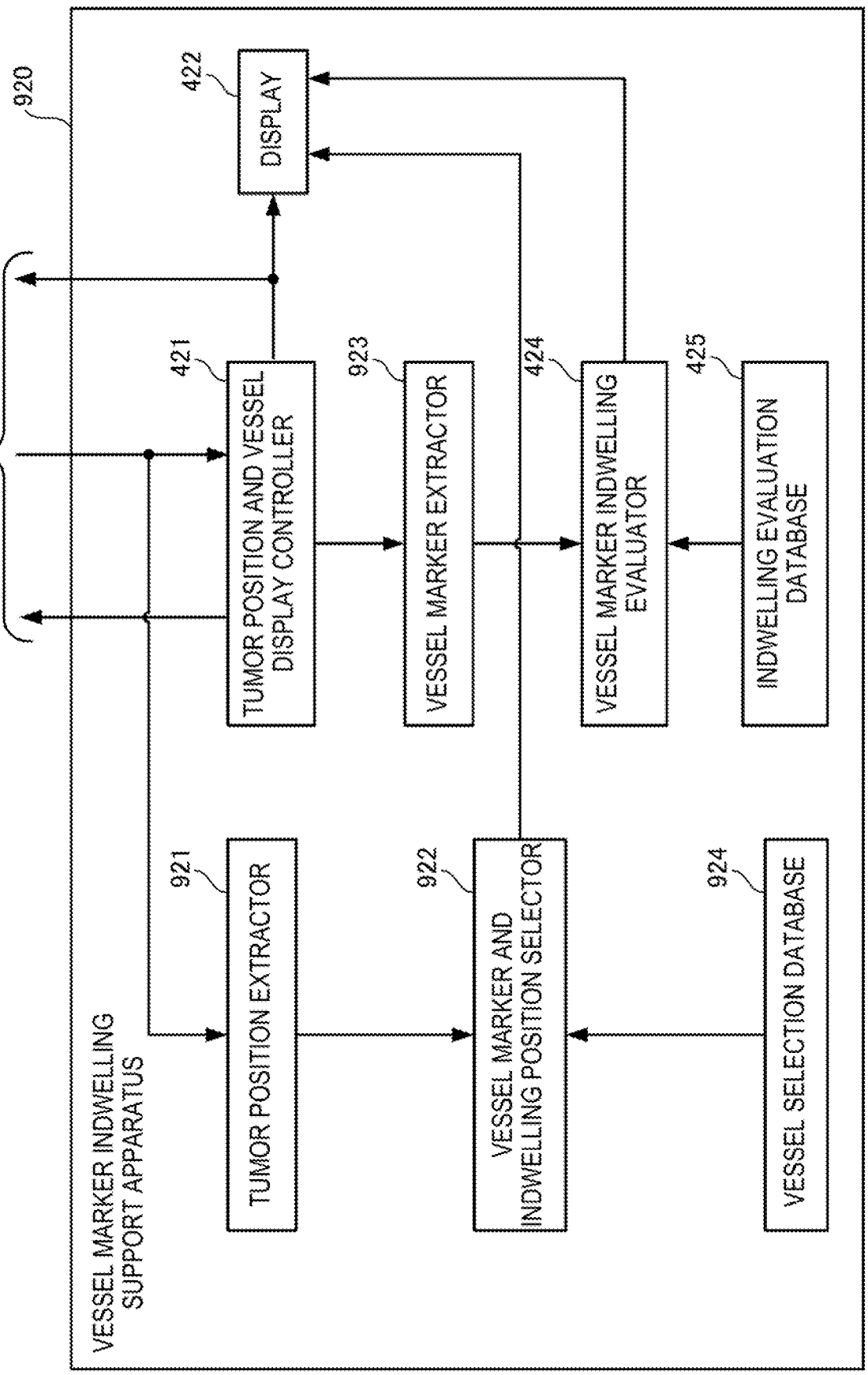
FIG. 9 is a block diagram showing the arrangement of a vessel marker indwelling support apparatus according to the third example embodiment of the present invention.

FIG. 9 is a block diagram showing the arrangement of a vessel marker indwelling support apparatus 920. Note that the same reference numerals as in FIG. 4 denote similar constituent elements in FIG. 9, and a repetitive explanation thereof will be omitted.

The vessel marker indwelling support apparatus 920 includes a tumor position extractor 921, a vessel marker and indwelling position selector 922, a vessel marker extractor 923, and a vessel selection database 924. Before a vessel marker indwelling treatment, the tumor position extractor 921 extracts a tumor position from an angiographic image (X-ray fluoroscopic image) from the treatment room 410. Before the vessel marker indwelling treatment, the vessel marker and indwelling position selector 922 refers to the vessel selection database 924, and selects an appropriate vessel marker and an appropriate vessel marker indwelling position in accordance with the tumor position. During the vessel marker indwelling treatment, the vessel marker extractor 923 extracts the vessel marker from the angiographic image from the treatment room 410.

(Vessel Selection Database)

FIG. 10 is a view showing the arrangement of the vessel selection database 924 according to this example embodiment. The vessel selection database 924 is referred to when the vessel marker and indwelling position selector 922 selects an appropriate vessel marker and an appropriate vessel marker indwelling position in accordance with the tumor position.

The vessel selection database 924 stores vessel marker indwelling information 1002, vessel marker indwelling information 1003, and vessel marker indwelling information 1004 in association with a tumor position 1001. The tumor position 1001 contains information of the affected part and the affected part position. Each of the vessel marker indwelling information 1002 to 1004 contains a vessel marker to be used, the name of a blood vessel for indwelling, and the range of indwelling.

<<Procedure of Vessel Marker Indwelling Support Apparatus>>

Figure 11:
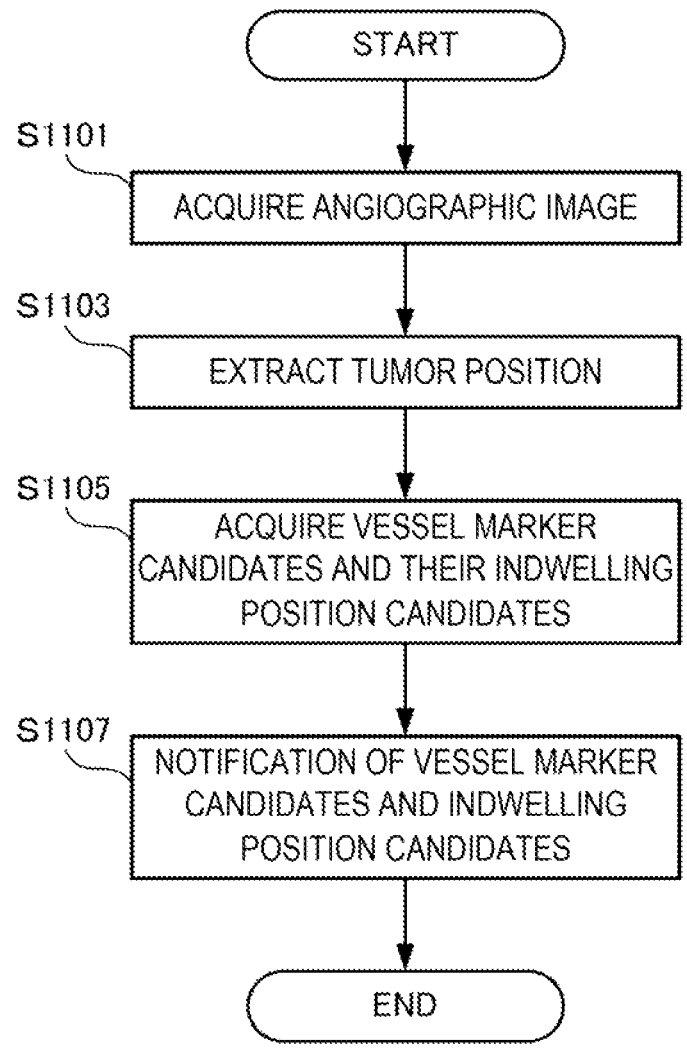
FIG. 11 is a flowchart showing the procedure of the vessel marker indwelling support apparatus according to the third example embodiment of the present invention.

FIG. 11 is a flowchart showing the procedure of the vessel marker indwelling support apparatus 920 according to this example embodiment. Note that FIG. 11 shows a flowchart of portions related to this example embodiment, and a repetitive explanation of processing will be omitted.

In step S1101, the vessel marker indwelling support apparatus 920 acquires an angiographic image. In step S1103, the vessel marker indwelling support apparatus 920 extracts a tumor position from the angiographic image. In step S1105, the vessel marker indwelling support apparatus 920 refers to the vessel selection database 924, and acquires vessel marker candidates and vessel marker indwelling position candidates. Then, in step S1107, the vessel marker indwelling support apparatus 920 performs notification of the vessel marker candidates and the vessel marker indwelling position candidates.

In this example embodiment, a vessel marker to be used and a position where the vessel marker is to be indwelled can easily be known based on the position of a tumor.

Fourth Example Embodiment

A radiotherapy system according to the fourth example embodiment of the present invention will be explained below. The radiotherapy system according to this example embodiment differs from the abovementioned second example embodiment in that the system includes an arrangement for discriminating a vessel marker for radiotherapy and automatically calculating an irradiation position. The rest of the arrangement and the operation are the same as the second example embodiment, so the same reference numerals denote similar arrangement and operation, and a detailed explanation thereof will be omitted.

<<Configuration of Radiotherapy System>>

Figure 12:
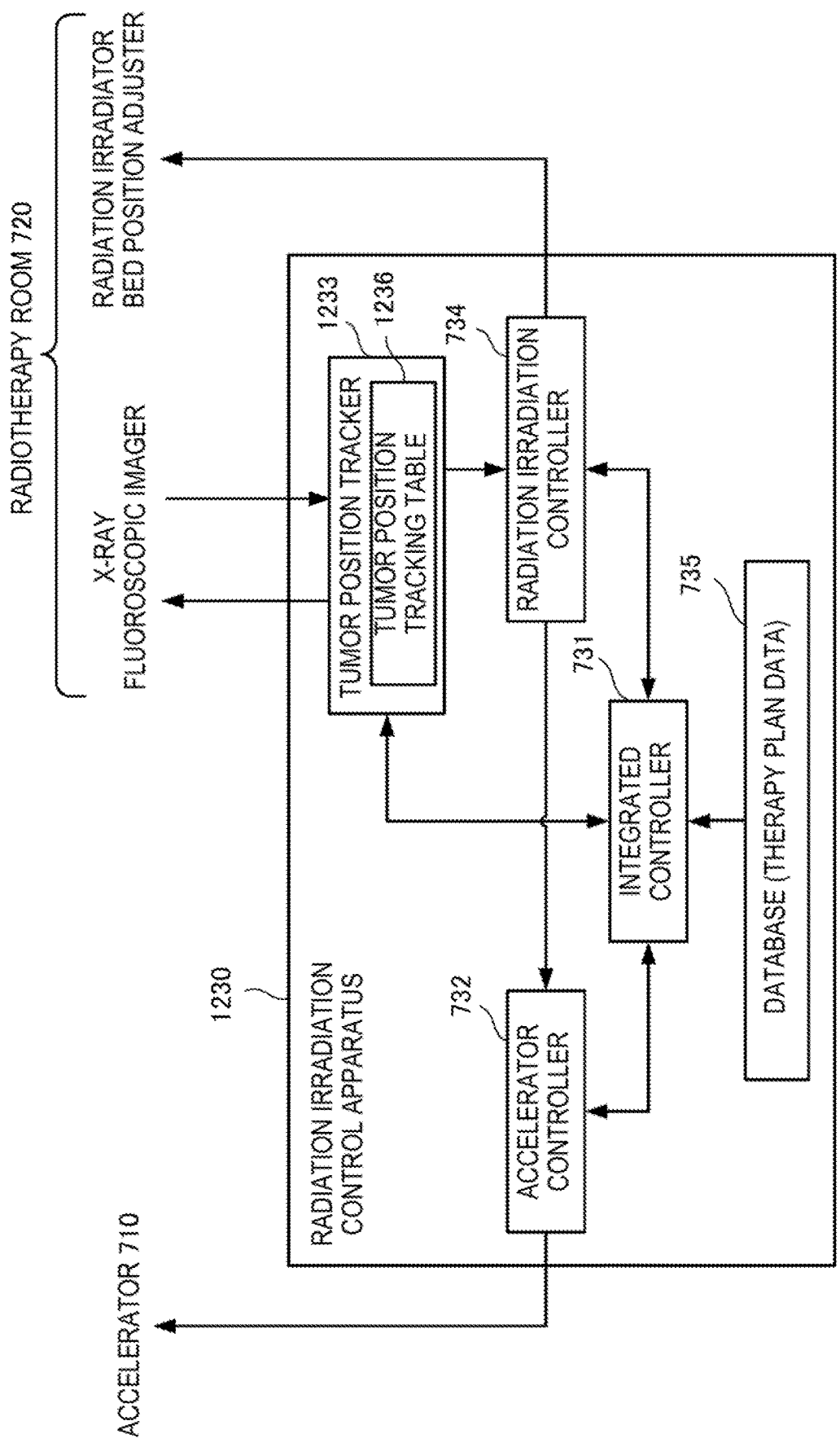
FIG. 12 is a block diagram showing the arrangement of a radiation irradiation control apparatus according to the fourth example embodiment of the present invention.

FIG. 12 is a block diagram showing the arrangement of a radiation irradiation control apparatus 1230 according to this example embodiment. Note that the same reference numerals as in FIG. 7 denote the same constituent elements in FIG. 12, and a repetitive explanation thereof will be omitted.

The radiation irradiation control apparatus 1230 includes a tumor position tracker 1233. The tumor position tracker 1233 includes a tumor position tracking table 1236, discriminates a vessel marker based on an X-ray fluoroscopic image from an X-ray fluoroscopic imager of a radiotherapy room 720, and tracks the tumor position. A radiation irradiation controller 734 is notified of this tumor position tracking information, and implements radiation irradiation to an accurate position that follows even successive changes in tumor position.

(Vessel Marker Discrimination Table)

FIG. 13 is a view showing the arrangement of the tumor position tracking table 1236 according to this example embodiment. When performing radiation irradiation, the tumor position tracker 1233 uses the tumor position tracking table 1236 in order to discriminate a vessel marker from an X-ray fluoroscopic image of the affected part from the radiotherapy room 720, and track the tumor position.

The tumor position tracking table 1236 includes a vessel marker table 1310 for discriminating a vessel marker, and a tumor position marker 1320) to be used to calculate the current tumor position from the discriminated vessel marker.

The vessel marker table 1310 stores a shape 1312, dimensions 1313, and image data 1314 of a vessel marker in association with a vessel marker ID 1311. Note that the image data 1314 may also be a feature amount extracted from image data. A vessel marker is discriminated by finding a shape corresponding to the image data 1314 from an X-ray fluoroscopic image.

The tumor position table 1320 stores tumor positions 1323 and bed positions 1324 calculated based on a predetermined number of discriminated vessel markers 1321 and three-dimensional positions 1322 thereof.

<<Procedure of Radiotherapy System>>

Figure 14:
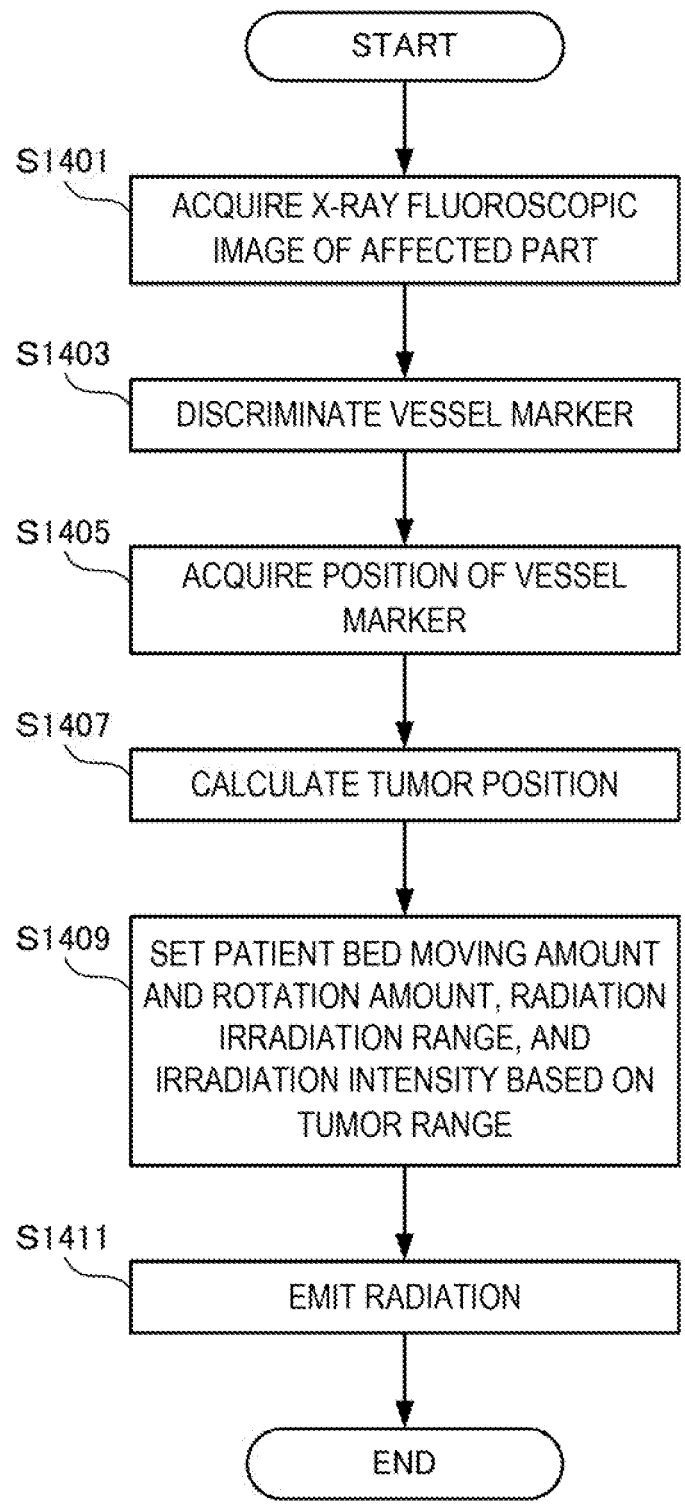
FIG. 14 is a flowchart showing the procedure of the radiation irradiation control apparatus according to the fourth example embodiment of the present invention.

FIG. 14 is a flowchart showing the procedure of the radiation irradiation control apparatus 1230 according to this example embodiment.

In step S1401, the radiation irradiation control apparatus 1230 acquires an X-ray fluoroscopic image of the affected part. In step S1403, the radiation irradiation control apparatus 1230 extracts a vessel marker by referring to the vessel marker table 1310. In step S1405, the radiation irradiation control apparatus 1230 acquires the position of the extracted vessel marker. Then, in step S1407, the radiation irradiation control apparatus 1230 calculates the current tumor position based on the position of the vessel marker.

In step S1409, the radiation irradiation control apparatus 1230 sets the moving amount and rotation amount of the patient bed, the irradiation range, and the irradiation intensity based on the calculated tumor position. In step S1411, the radiation irradiation control apparatus 1230 performs irradiation control for emitting radiation within the set irradiation range by the set irradiation intensity.

In this example embodiment, radiation irradiation can be automated by discriminating a vessel marker and tracking a tumor position.

Other Example Embodiments

In the above example embodiments, a term "vessel" is typified by a blood vessel such as an artery or a vein. However, the present invention has the same effect for another vessel as a metabolism path of an organ or a tissue such as lymph vessel. While the invention has been particularly shown and described with reference to example embodiments thereof, the invention is not limited to these example embodiments. It will be understood by those of ordinary skill in the art that various changes in form and details may be made therein without departing from the spirit and scope of the present invention as defined by the claims. A system or apparatus including any combination of the individual features included in the respective example embodiments may be incorporated in the scope of the present invention.

The present invention is applicable to a system including a plurality of devices or a single apparatus. The present invention is also applicable even when an information processing program, such as a radiation irradiation control program, for implementing the functions of example embodiments is supplied to the system or apparatus directly or from a remote site. Hence, the present invention also incorporates the program installed in a computer to implement the functions of the present invention by the computer, a medium storing the program, and a WWW (World Wide Web) server that causes a user to download the program. Especially, the present invention incorporates at least a non-transitory computer readable medium storing a program that causes a computer to execute processing steps included in the above-described example embodiments.

The invention claimed is:

1. A vessel fiducial marker for distinguishing an area in a body to be irradiated during radiotherapy, and for staying at a desired position only in a vessel,
    wherein the vessel fiducial marker has a one-stroke three-dimensional curved shape selected from an S shape, a figure 8 shape, an arc shape having at least two arcs forming a surface of a sphere, a twisted S shape, or a twisted figure 8 shape in order to discriminate from a living tissue,
    wherein the vessel fiducial marker is made from a single linear member of metal wire material absorbing radiation,
    wherein the vessel fiducial marker has a deformation fixed shape for engaging with an inner wall of the vessel by deformation such that the vessel fiducial marker stays at the desired position in the vessel, and
    wherein the vessel fiducial marker after deformation has a diameter that matches a diameter of the vessel.

2. The vessel fiducial marker for radiotherapy according to claim 1, comprising a shape memory material.

3. The vessel fiducial marker for radiotherapy according to claim 1, comprising a nonmagnetic material that reduces metal artifact.

4. The vessel fiducial marker for radiotherapy according to claim 1, wherein, once inserted, the vessel marker remains in a vessel without embolization.

5. A radiotherapy support method comprising:
    inserting a vessel fiducial marker for distinguishing an area in a body to be irradiated during radiotherapy, and for staying at a desired position only in a vessel, and engaging the vessel fiducial marker with an inner wall of the vessel by deforming the vessel fiducial marker;
    performing X-ray imaging on a living body region containing the vessel fiducial marker fixed in the vessel; and
    performing notification of a radiation irradiation range based on a position of the imaged vessel fiducial marker,
    wherein the vessel fiducial marker has a one-stroke three-dimensional curved shape selected from an S shape, a figure 3 shape, a figure 8 shape, an arc shape having at least two arcs forming a surface of a sphere, a twisted S shape, or a twisted figure 8 shape in order to discriminate from a living tissue, and
    wherein the vessel fiducial marker is made from a single linear member of metal wire material absorbing radiation.

6. The radiotherapy support method according to claim 5, wherein the vessel fiducial marker comprises a shape memory material.

7. The radiotherapy support method according to claim 5, wherein the vessel fiducial marker comprises a nonmagnetic material that reduces metal artifact.

8. A radiation irradiation control apparatus comprising:
    an image sensor, a controller, and an adjustable platform for placing a patient thereon;
    wherein
    the image sensor is configured to perform an X-ray imaging on a body region of the patient, wherein the body region contains a vessel fiducial marker for distinguishing an area in a body to be irradiated during radiotherapy, and for staying at a desired position only in a vessel;
    the controller is configured to:
    calculate a radiation irradiation range based on a position of the imaged vessel fiducial marker;
    adjust a position and a direction of the patient on the platform in accordance with the calculated range; and
    perform a radiotherapy process on the patient according to the range after the position and the direction of the patient are adjusted,
    wherein the vessel fiducial marker has a one-stroke three-dimensional curved shape selected from an S shape, a figure 3 shape, a figure 8 shape, an arc shape having at least two arcs forming a surface of a sphere, a twisted S shape, or a twisted figure 8 shape in order to discriminate from a living tissue, and
    wherein the vessel fiducial marker is made from a single linear member of metal wire material absorbing radiation.

9. The radiation irradiation control apparatus according to claim 8, wherein the vessel fiducial comprises a shape memory material.

10. The radiation irradiation control apparatus according to claim 8, wherein the vessel fiducial marker comprises a nonmagnetic material that reduces metal artifact.

11. A vessel fiducial marker indwelling support apparatus for indwelling a vessel fiducial marker for distinguishing an area in a body to be irradiated during radiotherapy, and for staying at a desired position only in a vessel, comprising:
    a storage medium that stores information of a tumor position, a vessel fiducial marker to be used, and at least two vessels in which the vessel fiducial marker is to be indwelled, in association with each other; and
    a processor that refers to the storage based on the tumor position as a target of radiotherapy, and determines the vessel fiducial marker to be used and the at least two vessels in which the vessel fiducial marker is to be indwelled;
    wherein the vessel fiducial marker has a one-stroke three-dimensional curved shape selected from an S shape, a figure 3 shape, a figure 8 shape, an arc shape having at least two arcs forming a surface of a sphere, a twisted S shape, or a twisted figure 8 shape in order to discriminate from a living tissue, and
    wherein the vessel fiducial marker is made from a single linear member of metal wire material absorbing radiation.

12. The vessel fiducial marker indwelling support apparatus according to claim 11, wherein the vessel fiducial marker comprises a shape memory material.

13. The vessel fiducial marker indwelling support apparatus according to claim 11, wherein the vessel fiducial marker comprises a nonmagnetic material that reduces metal artifact.

\* \* \* \* \*